US011207474B2

(12) United States Patent
Dunne

(10) Patent No.: US 11,207,474 B2
(45) Date of Patent: Dec. 28, 2021

(54) DRUG DELIVERY DEVICE

(71) Applicant: Boehringer Ingelheim International GmbH, Ingelheim am Rhein (DE)

(72) Inventor: Stephen Terence Dunne, Ipswich (GB)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 781 days.

(21) Appl. No.: 15/327,836

(22) PCT Filed: Jul. 24, 2015

(86) PCT No.: PCT/EP2015/001534
§ 371 (c)(1),
(2) Date: Jan. 20, 2017

(87) PCT Pub. No.: WO2016/012102
PCT Pub. Date: Jan. 28, 2016

(65) Prior Publication Data
US 2017/0203056 A1      Jul. 20, 2017

(30) Foreign Application Priority Data

Jul. 25, 2014   (GB) ...................................... 1413181

(51) Int. Cl.
*A61M 11/00*       (2006.01)
*A61M 15/00*       (2006.01)
(Continued)

(52) U.S. Cl.
CPC ........ *A61M 11/007* (2014.02); *A61M 15/002* (2014.02); *B05B 11/0054* (2013.01);
(Continued)

(58) Field of Classification Search
CPC .. A61M 11/00; A61M 11/006; A61M 11/007; A61M 11/06; A61M 15/00;
(Continued)

(56) References Cited

U.S. PATENT DOCUMENTS

| 4,623,337 A | 11/1986 | Maurice |
| 5,547,131 A * | 8/1996 | Brace ................ A61M 15/0065 128/200.23 |

(Continued)

FOREIGN PATENT DOCUMENTS

| EP | 2614848 A1 | 7/2013 |
| JP | 2007522902 A | 8/2007 |

(Continued)

OTHER PUBLICATIONS

International Search Report for corresponding PCT Application No. PCT/EP2015/001534, 6 pages, dated Nov. 5, 2015.

*Primary Examiner* — Justine R Yu
*Assistant Examiner* — Matthew D Ziegler
(74) *Attorney, Agent, or Firm* — Matthew B. Dernier, Esq.

(57) ABSTRACT

A drug delivery device, in particular a nebulizer or inhaler, for dispensing a fluid includes a cartridge having a collapsible container within which the fluid is disposed, a mechanism to help the collapsing process and to prevent the collapsed container from expanding again, hence preventing the forming of vapor and gas bubbles within, where the mechanism is adapted to pressurize the fluid within the container during withdrawal of the fluid.

20 Claims, 17 Drawing Sheets

(51) Int. Cl.
  *B05B 11/00* (2006.01)
  *A61M 16/20* (2006.01)
(52) U.S. Cl.
  CPC .... *B05B 11/00416* (2018.08); *A61M 15/0021* (2014.02); *A61M 16/209* (2014.02); *A61M 2202/0468* (2013.01); *A61M 2205/273* (2013.01); *B05B 11/0038* (2018.08); *B05B 11/3091* (2013.01)
(58) Field of Classification Search
  CPC ............ A61M 15/002; A61M 15/0021; A61M 16/00; A61M 16/08; A61M 16/0875; A61M 16/20; A61M 16/208; A61M 16/209; A61M 2202/04; A61M 2202/0468; A61M 2205/0216; A61M 2205/19; A61M 2205/27; A61M 2205/273; A61M 2210/06; A61M 2210/0625; B05B 11/00–3098
  See application file for complete search history.

(56) References Cited

U.S. PATENT DOCUMENTS

| | | | |
|---|---|---|---|
| 5,662,271 A | 9/1997 | Weston | |
| 5,950,619 A | 9/1999 | Van der Linden | |
| 6,223,933 B1* | 5/2001 | Hochrainer | B05B 11/00412 220/723 |
| 6,302,101 B1* | 10/2001 | Py | A61M 11/06 128/200.22 |
| 6,401,984 B1 | 6/2002 | Jumel | |
| 6,401,987 B1 | 6/2002 | Oechsel | |
| 6,708,846 B1 | 3/2004 | Karl-Heinz | |
| 6,736,796 B2* | 5/2004 | Shekalim | A61M 5/1454 251/129.01 |
| 7,571,722 B2 | 8/2009 | Wuttke | |
| 8,550,300 B2* | 10/2013 | Lee | B05B 11/3074 222/95 |
| 9,550,025 B2* | 1/2017 | Dunne | A61M 5/2425 |
| 2005/0183718 A1 | 8/2005 | Wuttke | |
| 2012/0090603 A1* | 4/2012 | Dunne | A61M 11/06 128/200.22 |
| 2013/0041241 A1 | 2/2013 | Felts | |
| 2015/0144127 A1* | 5/2015 | Ekman | B05B 11/0054 128/200.14 |
| 2016/0167071 A1* | 6/2016 | Baillet | A61M 11/02 222/23 |

FOREIGN PATENT DOCUMENTS

| | | |
|---|---|---|
| WO | 1996006011 A2 | 2/1996 |
| WO | 0010630 A1 | 3/2000 |
| WO | 0047332 A1 | 8/2000 |
| WO | 0170309 A1 | 9/2001 |
| WO | 2005079997 A1 | 9/2005 |
| WO | 2009115200 A1 | 9/2009 |
| WO | 2010094305 A1 | 8/2010 |
| WO | 2011003979 A1 | 1/2011 |
| WO | 2011117592 A1 | 9/2011 |
| WO | 2012096889 A1 | 7/2012 |
| WO | 2012162305 A1 | 11/2012 |
| WO | 2013163088 A1 | 10/2013 |
| WO | 2016012102 A1 | 1/2016 |

* cited by examiner

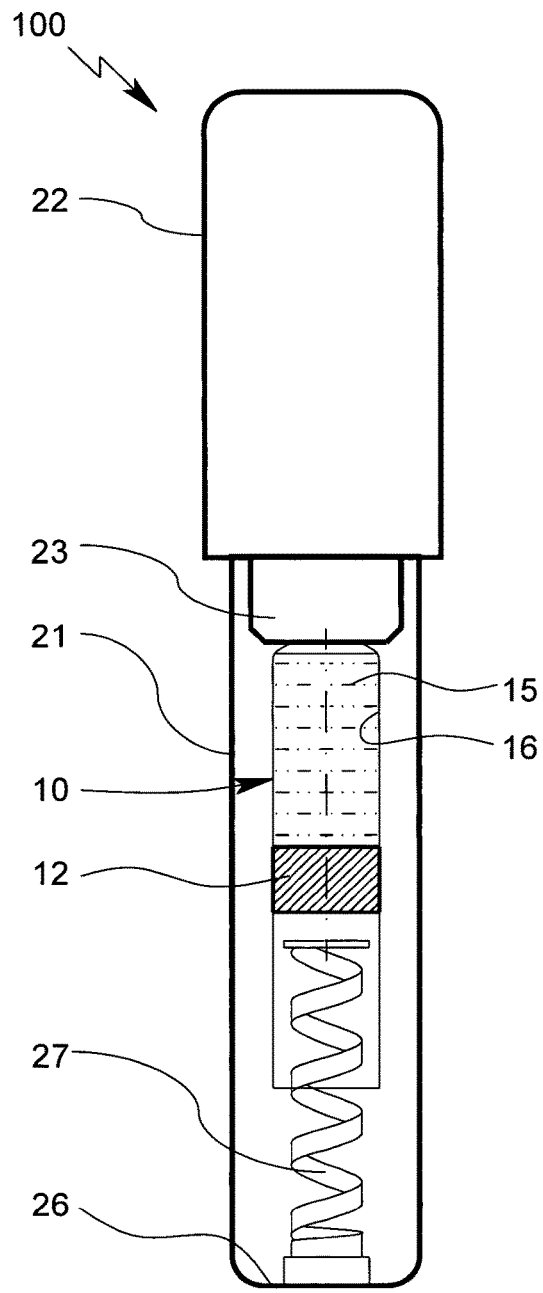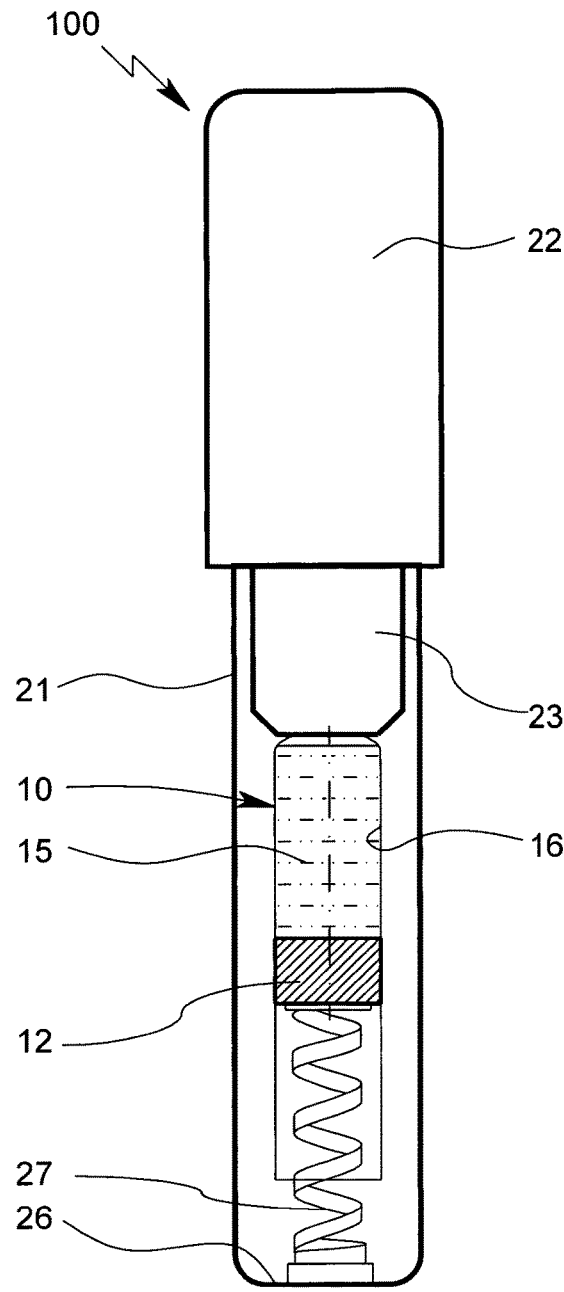
Fig. 3a                    Fig. 3b

DRUG DELIVERY DEVICE

The present invention relates to a cartridge for storing a drug solution or suspension within a portable nebulizer or inhaler or any other drug delivery device. In particular, the present invention relates to a drug delivery device, preferably a nebulizer or an injector, according to the preamble of claim 1.

When a liquid drug is drawn from a cartridge with a collapsible/compressible container, e.g. sucked into a nebulizer or the like, negative pressure might occur in the container and can lead to undesired formation of vapor and gas bubbles in the container and/or the drug delivery device. This applies particularly to liquids with low vapor pressure, in particular ethanol based solutions.

WO 2010/094305 A1 relates to a device, a cartridge and a method for dispensing a liquid, wherein the liquid is pressurized in a cartridge to a first lower pressure and, then, pressurized in doses by a pump to a second higher pressure. A valve arranged between the cartridge and the pump is normally closed and/or opened only temporarily.

When the container or its content is pressurized from outside, e.g. by pressurizing means as disclosed in WO 2010/094305 A1, to facilitate withdrawal/suction of liquid, this may lead to undesired leakage from the container during non-use.

Object of the invention is to provide a drug delivery device or cartridge assembly, wherein withdrawal/suction of liquid from a collapsible/compressible container is facilitated, while undesired leakage during non-use can be prevented or minimized.

The above object is achieved by a drug delivery device according to claim 1. Preferred embodiments are subject of the subclaims.

According to one aspect of the present invention a collapsible/compressible container is combined with a mechanism, in particular an air spring and/or a friction engagement and/or a ratchet arrangement, to support the collapsing/compressing process, in particular pushing a cartridge plunger or piston, and/or to prevent the collapsed/compressed container expanding again, hence preventing the formation of vapor and gas bubbles within.

The collapsible/compressible container may be a movable piston/cylinder arrangement or a collapsible bag such as a bellows and/or enclosed or defined or determined by a movable piston/cylinder arrangement or a collapsible bag such as a bellows, preferably wherein the movable piston/cylinder arrangement or collapsible bag is associated with a cartridge of the drug delivery device.

In particular, the container is or has a volume, preferably enclosed or defined or determined by a movable piston/cylinder arrangement or a collapsible bag such as a bellows.

Preferably, collapsible/compressible should be understood as the ability to change the volume of said container or cartridge. In particular, the volume determined or enclosed by the container or cartridge is variable/changeable, preferably by said mechanism. Particularly preferred, the volume can be reduced by collapsing/compressing the container or cartridge at least partially, preferably by moving at least one part or component, e.g. the piston of the piston/cylinder arrangement or a wall, of the container or cartridge inwards. Preferably the volume determined or enclosed by the container or cartridge is (automatically or repeatedly or constantly) adjusted to the preferably liquid content of the container or cartridge.

The present invention is particularly useful when used in combination with portable nebulizers such as the type described in prior art U.S. Pat. No. 5,662,271 or any other device. In such devices it is important that gas or vapor bubble formation is kept to a minimum. Otherwise an overfill of the container may be required and a certain orientation of the device when loading the piston/cylinder chamber may be required to ensure that no gas/vapor is sucked into the dosing chamber ensuring that the dose of liquid is always the same.

The cartridge may be based on a standard injection cartridge such as those used for insulin and dental anesthetics or a collapsible bag type container such as a bellows. It incorporates a mechanism to push a cartridge plunger or stopper or help collapse a collapsible bag when fluid is being withdrawn from the cartridge in particular into an inhaler, hence pressurizing or preventing a vacuum or negative pressure forming within the cartridge when the contents are being withdrawn.

According to another aspect of the present invention the drug delivery device and/or its mechanism is adapted to pressurize the content in the container temporarily, in particular—at least essentially only—during withdrawal of the content from the container, preferably wherein the withdrawal of the content precedes the delivery of the fluid, in particular a drug dose, to a user or patient.

Preferably, the drug delivery device and/or its mechanism to pressurize the content of the container or cartridge is adapted to decrease/reduce the pressure generated by the mechanism—in particular at least essentially to ambient pressure—after withdrawal of the content and/or of a predetermined amount, in particular a drug dose, therefrom and/or during non-use of the—in particular (already) tensioned—drug delivery device, in particular automatically and/or continuously, particularly preferred via an air leak pathway and/or a non-return valve. In this way, undesired leakage from the container during non-use of the device is prevented or at least minimized. Furthermore, the requirements for the tightness of other components of the drug delivery device can be reduced.

Preferably, the pressure of the container or its content is decreased during non-use of the nebulizer/inhaler, in particular at least essentially to ambient pressure.

Preferably, the contents are only pressurized during the withdrawal of the contents and/or of a predetermined amount, in particular a drug dose, therefrom. This prevents the piston getting stuck due to static friction and in the case of a collapsible bag or bellows helps the collapsible bag to collapse preventing gas migration through the walls as the cartridge contents are not subjected to a negative pressure.

The invention consists of or provides a collapsible container combined with a mechanism to help the collapsing process and prevent the collapsed container expanding again hence preventing the formation of vapor and gas bubbles within. The collapsible container may be a movable piston/cylinder arrangement or a collapsible bag such as a bellows.

The advantages of the present invention are numerous.

The undesired formation of vapor and gas/air bubbles within the container and/or the drug delivery device can be prevented or minimized.

Since the container has no significant air bubbles it can be used in any orientation when dosing the device making it easier to use and less likely to be misused.

Further, the liquid can be drawn from any location within the container, e.g. from its bottom or top, via a tube or an opening.

Further, the pressurization of the liquid in the container facilitates the filling of the pump and/or fluidic connections with liquid, in particular when using the device for the first time or after longer periods of non-use. Thus, priming (operation to fill the pump and fluidic connections with liquid) can be avoided or at least minimized.

Further, there is no need to significantly overfill the cartridge. Overfill can lead to patient misuse if the user can access this.

Specific embodiments of the invention will now be described with reference to the figures. It shows:

FIG. 1 a schematic section of a cartridge;

FIG. 2a a schematic section of a cartridge assembly or drug delivery device in a rest position;

FIG. 2b a schematic section of the cartridge assembly or drug delivery device according to FIG. 2a in a cocked/tensioned position;

FIG. 3a a schematic section of a cartridge assembly or drug delivery device in a rest position;

FIG. 3b a schematic section of the cartridge assembly or drug delivery device according to FIG. 3a in a cocked/tensioned position;

FIG. 4a a schematic section of a cartridge assembly or drug delivery device according to a first embodiment of the present invention in a rest position;

FIG. 4b a schematic section of the cartridge assembly or drug delivery device according to FIG. 4b in a cocked/tensioned position;

FIG. 4c a schematic section of a cartridge assembly or drug delivery device according to a second embodiment of the present invention in a rest position;

FIG. 4d a schematic section of the cartridge assembly or drug delivery device according to FIG. 4c in a cocked/tensioned position;

FIG. 5a a schematic section of the cartridge assembly or drug delivery device of FIG. 4a, but with the cartridge being almost empty;

FIG. 5b a schematic section of the cartridge assembly or drug delivery device of FIG. 4b, but with the cartridge being almost empty;

FIG. 6a a schematic section of a mechanism to help collapsing the container according to the present invention;

FIG. 6b a schematic section of the mechanism to help collapsing the container according to another embodiment;

FIG. 6c a schematic section of the mechanism to help collapsing the container according to a further embodiment;

FIG. 6d a schematic section of a mechanism to help collapsing the container according to a third embodiment of the present invention in a state when firing or nebulizing the associated cartridge or drug delivery device;

FIG. 6e a schematic section of the mechanism according to FIG. 6d in a state when cocking or tensioning the associated cartridge or drug delivery device;

FIG. 7a a schematic section of a cartridge assembly or drug delivery device with the mechanism according to FIG. 6d in a rest position;

FIG. 7b a schematic section of the prior art cartridge assembly or drug delivery device with the mechanism according to FIG. 6d in a cocked/tensioned position;

FIG. 8a a schematic section of a cartridge (assembly) according to a fourth embodiment of the present invention;

FIG. 8b a schematic section of the drug delivery device with the cartridge (assembly) of FIG. 8a according to the fourth embodiment in a rest position;

FIG. 8c a schematic section explaining the operation of the cartridge assembly or drug delivery device according to FIG. 8b;

FIG. 9a a schematic section of the cartridge assembly or drug delivery device of FIG. 8b in a rest position or uncocked/released position but with the container remove collapsed;

FIG. 9b a schematic section of the cartridge assembly or drug delivery device of FIG. 9a in a cocked/tensioned position;

FIG. 9c a schematic section of the cartridge assembly or drug delivery device of FIG. 9a, but with the container more collapsed;

FIG. 11b shows a schematic enlargement of the encircled area of FIG. 11a;

FIG. 11c shows a schematic enlargement of the encircled area of FIG. 11a;

Figure 12A:
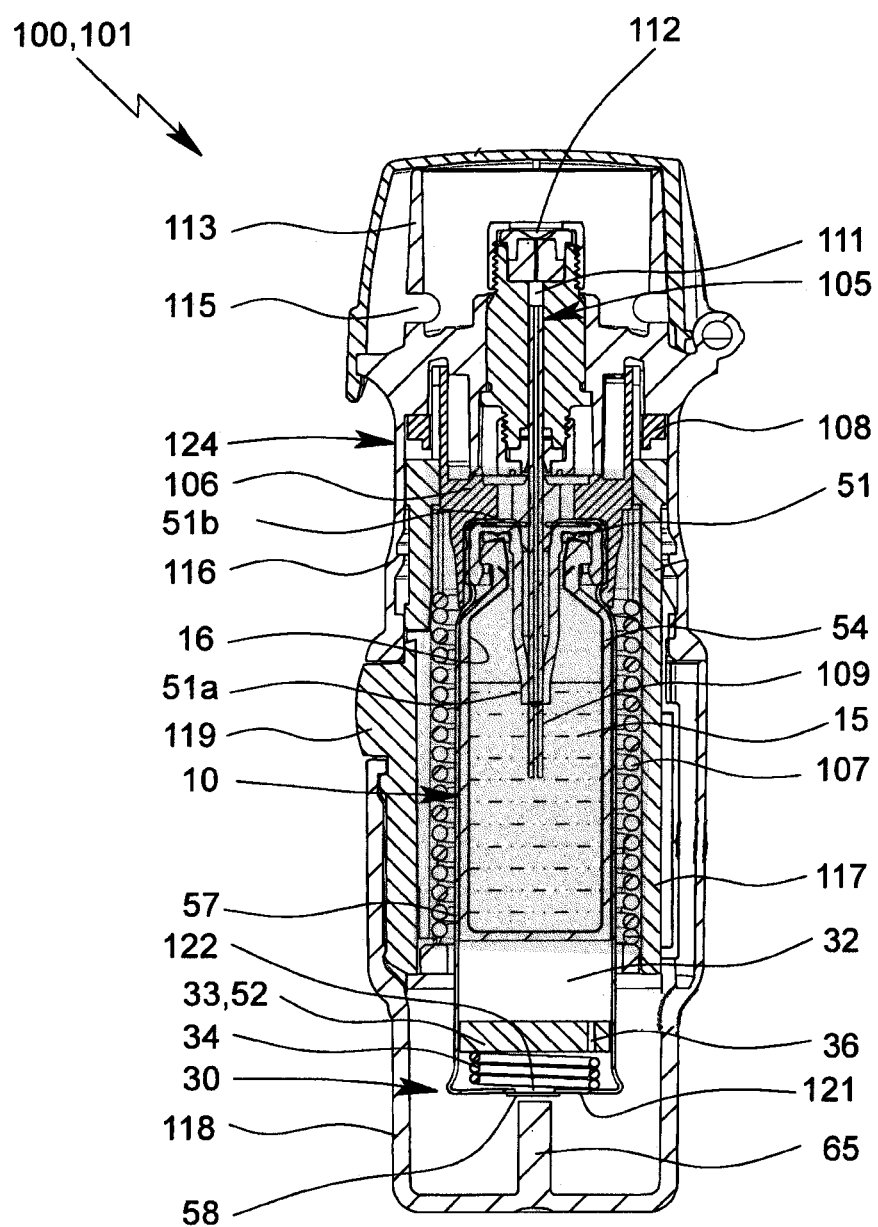
Figure 12B:
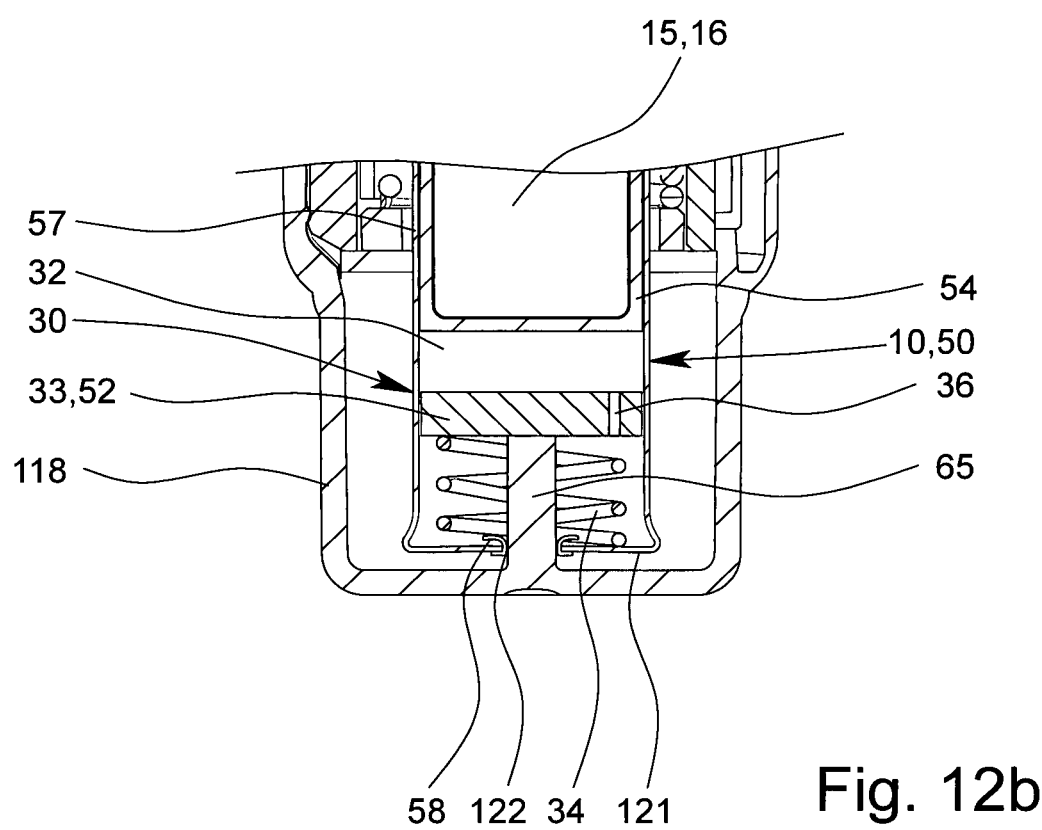

FIG. 12a a schematic section of a cartridge assembly or drug delivery device according to a fifth embodiment of the present invention in a rest position; and FIG. 12b a schematic enlargement of the lower part of the cartridge assembly or drug delivery device according to FIG. 12a, but in a cocked/tensioned position.

In the Figures, the same reference numerals are used for identical or similar parts, resulting preferably in corresponding or comparable properties and advantages, even if the associated description is not repeated.

Figure 1:
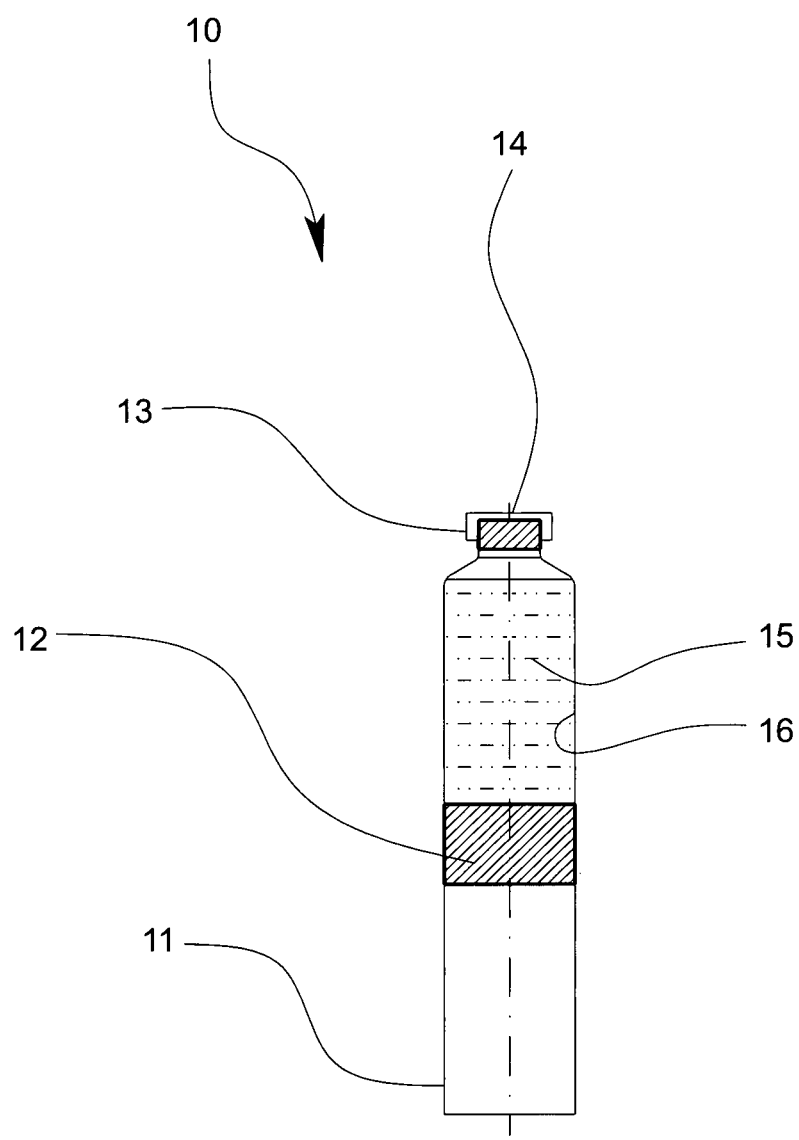

FIG. 1 illustrates a standard cartridge 10 used in the pharmaceutical industry, for example for dental injections and insulin injections. A cartridge body or barrel 11 or container 16 here preferably has or contains a liquid drug solution or suspension, called liquid 15, within. The liquid 15 is contained within a cartridge chamber or container 16, here preferably defined by a movable piston or stopper 12 at one end (towards a proximal end of the cartridge) and a container closure or seal preferably in the form of a rubber seal or septum 14 often held into place by a metal crimp 13 at the other end (a distal end of the cartridge). The barrel 11 is open at its proximal end 16.

Figure 2A:
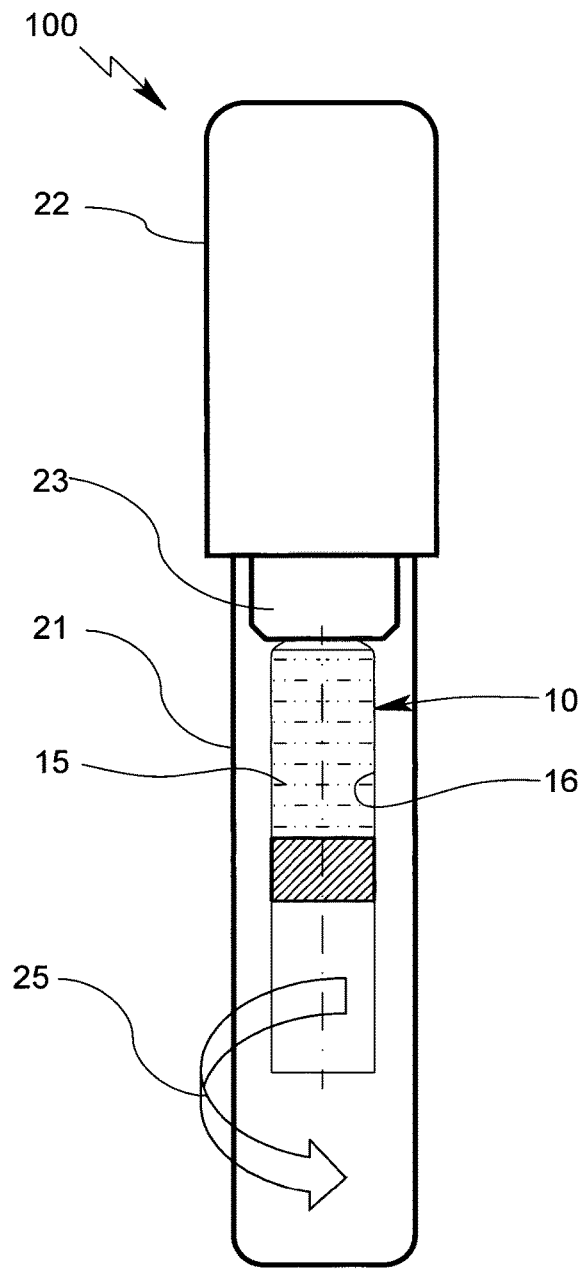
Figure 2B:
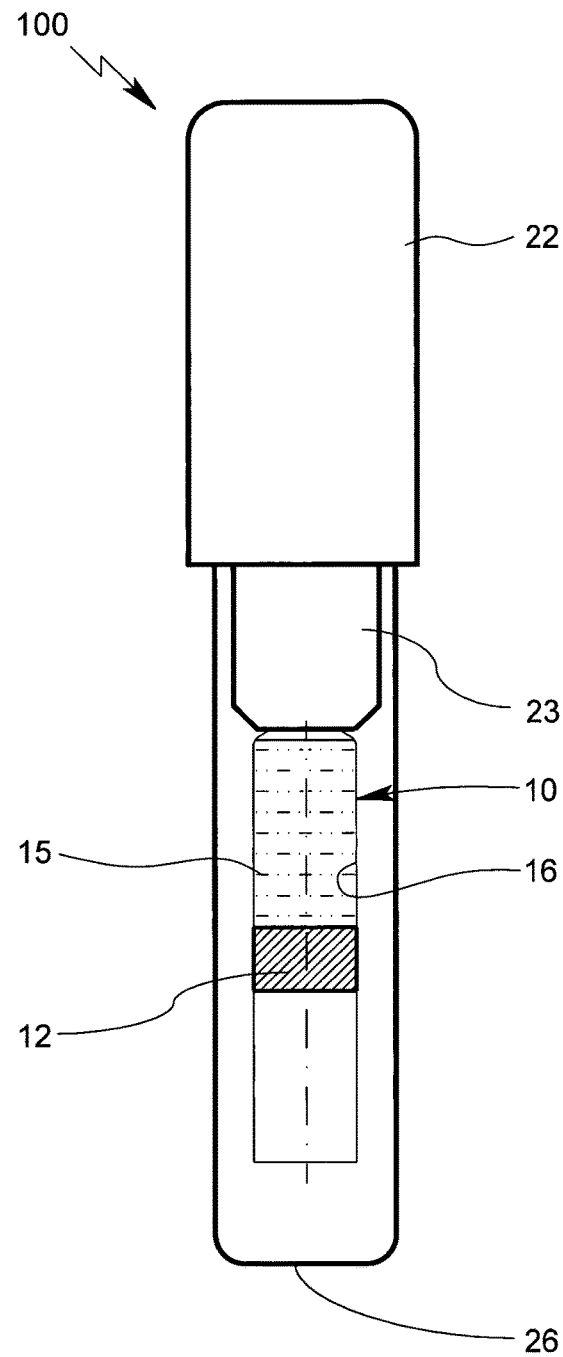

FIGS. 2a and 2b show a cartridge assembly or drug delivery device 100, in particular a nebulizer or inhaler, with cartridge 10. The cartridge 10 is connected or fixed to a connector 23 preferably wherein the connector 23 has a sharp ended tube or needle (not shown) pierced through the septum 14 shown in FIG. 1 making fluid communication preferably via a non-return valve to a pump or piston cylinder arrangement within the drug delivery device or inhaler. Preferably, the drug delivery device 100 is designed as a nebulizer 101 as explained later with reference to FIG. 12a and FIG. 12b.

In FIG. 2a the device 100 is in its rest position. In FIG. 2b the device 100 is in its cocked/tensioned position and ready to deliver a drug dose, e.g. in form of an atomized spray.

Preferably, the cartridge 10 or the container 16 contains several drug doses to be delivered to a user/patient. In particular, the drug delivery device 100 is adapted to be used multiple times with the same cartridge 10 or container 16.

Preferably, by twisting a bottom case 21 relative to top casing 22, as shown by arrow 25, the cartridge 10 moves down relative to casing 22 and closer to the bottom 26 of case 21 and/or the piston of said piston/cylinder arrangement (not shown) moves relative to the cylinder of said piston cylinder arrangement creating a vacuum or negative pressure and hence sucking/withdrawing contents of cartridge 10 or container 16 into the volume created.

Preferably, the (partial) vacuum or negative pressure created causes the piston or stopper 12 to move upwards relative to the cartridge body 11 and/or towards connector 23.

The problem with the arrangement shown in FIG. 2a and FIG. 2b is that the piston or stopper 12 movement is dependent on the negative pressure created in the cylinder or device 100 and this is sometimes not sufficient to overcome friction between the piston 12 and barrel 11 leading to gas and vapor bubble formation within cartridge 10 or container 16 and/or device 100.

FIGS. 3a and 3b show another arrangement of device 100 where the cartridge 10 or its content or container 16 is pressurized when ready to be used. A spring 27 exerts a force on piston 12 when the device 100 is cocked and the cartridge 10 is in its lower position as shown in FIG. 3b. This arrangement has the drawback that the contents are always pressurized after the device 100 is cocked—thus, the cylinder or pump of the device 100 is full of drug solution or liquid 15—with the consequence that if the user leaves the device 100 in the cocked position the liquid contents can leak out of a spray nozzle of the device 100. Such a device is described, e.g. in WO 2011/117592 A1 where a complex valve is employed to prevent liquid flow to a dosing chamber when the device is left in the cocked position.

Preferably the cocked/tensioned position or state refers to a position or state of the device 100 in which the device 100 is ready for drug delivery and/or the device 100 can be operated in order to deliver the fluid, here the liquid 15, in particular a drug dose.

In particular, in the cocked/tensioned position or state a certain amount, i. e. volume and/or mass, of the content and/or at least one drug dose has been withdrawn from the container 16. The amount of the content that has been withdrawn can preferably be delivered as a drug dose to a patient/user.

Figure 4A:
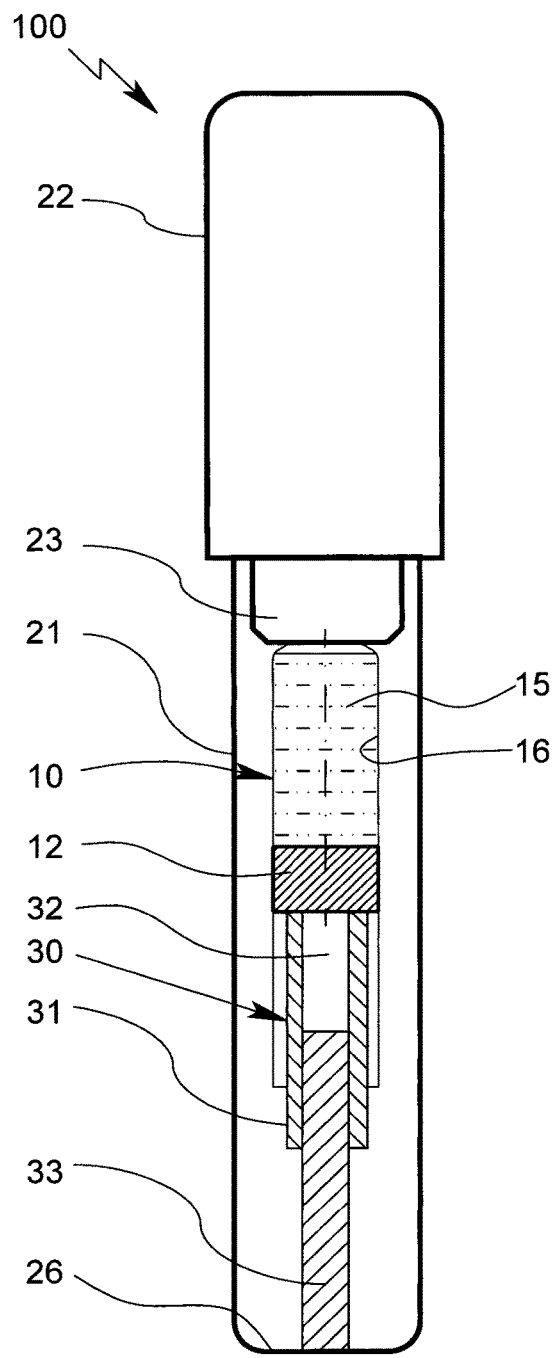
Figure 4B:
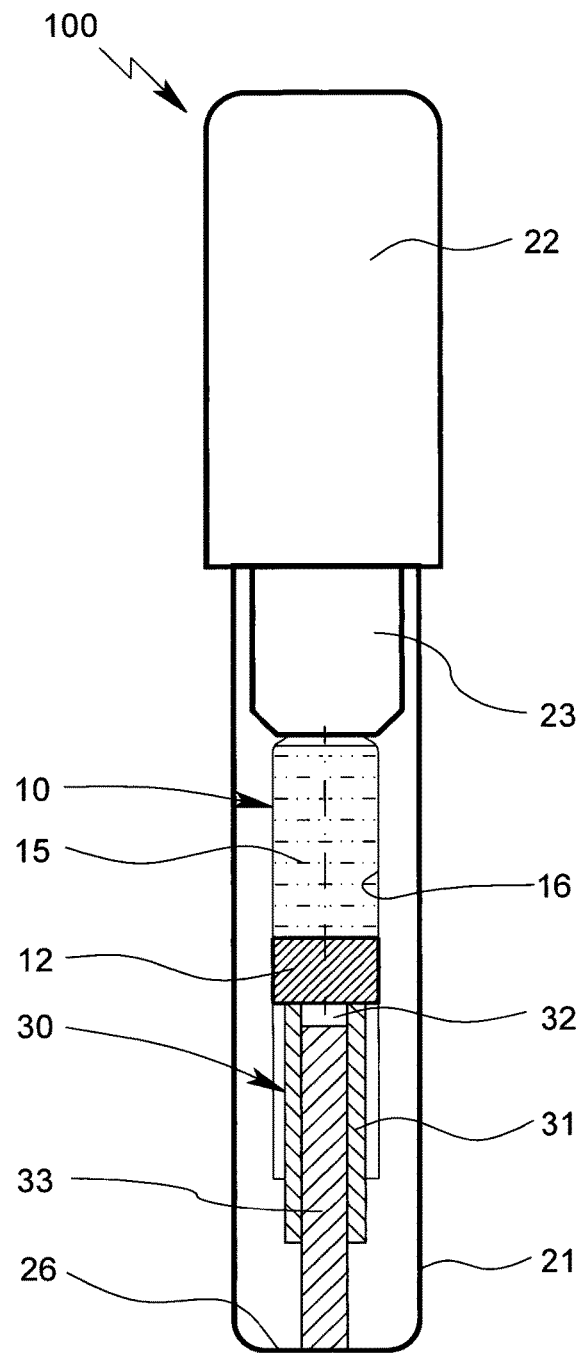

In FIGS. 4a and 4b a first embodiment of the invention is shown. In this embodiment, the cartridge assembly or drug delivery device 100 comprises a mechanism 30 to help collapse the collapsible container 16 or to pressurize the container 16 or liquid 15 and/or to push plunger or piston 12 associated to the cartridge 10 or container 16.

Preferably, the mechanism 30 is adapted to increase the pressure on the content in the container 16 during withdrawal of the content and/or of a certain amount and/or at least a drug dose therefrom, in particular in order to prevent or minimize undesired formation of vapor and gas bubbles in the container 16 and/or to help collapsing the container 16 and/or to push plunger or piston 12.

Optionally, the mechanism 30 is adapted to compensate—at least essentially—the pressure difference between the content, in particular liquid 15, in the container 16 and its environment and/or between the content, in particular liquid 15, in the container 16 and the atmosphere after firing/actuating the device 100 and/or during non-use of the device 100, in particular in order to prevent or minimize undesired formation of vapor and gas bubbles in the container 16 and/or device 100 and/or undesired leakage of the content, in particular liquid 15, as described further below.

Preferably, the mechanism 30 comprises or forms an air spring. The air spring is formed by a cylinder 31, a piston 33 and/or an air cavity 32. When the device 100 is cocked/tensioned as shown in FIG. 4b the air trapped in cavity 32 is compressed exerting a force on stopper or piston 12 and, hence, pressurizing the cartridge 10 contents, i. e. the liquid 15.

Preferably, the device 100, in particular the mechanism 30, comprises a gap or passageway.

The gap or passageway preferably creates an air leak pathway and/or allows the air trapped in cavity 32 to leak out and/or to flow into the ambient (atmosphere) reducing the pressure in the cavity 32, preferably back to ambient pressure, and, hence, eliminating or reducing the force exerted on piston 12. In this way, e.g. if the user leaves the device 100 cocked, the pressure in the cartridge 10 or on liquid 15 will be reduced, preferably at least essentially to ambient pressure, and possible leakage of liquid 15 can be prevented or minimized.

Alternatively or in addition, gap or passageway comprises a valve, in particular a non-return valve, and/or a valve, in particular a non-return valve, creates or forms the gap or passageway, in particular the air leak pathway. Preferably the valve controls the air flow through the gap or passageway, in particular in one direction or both directions.

In a preferred embodiment (not shown), the device 100, in particular the mechanism 30, comprises more than one, preferably two, gaps or passageways, preferably wherein each gap or passageway comprises a valve, in particular a non-return valve.

Preferably, the mechanism 30, in particular the gap or passageway, is adapted to decrease the pressure on the content and/or in the air cavity 32 after withdrawal of the content and/or during non-use of the—preferably tensioned—drug delivery device 100, in particular at least essentially to ambient pressure.

Optionally, the mechanism 30, in particular the gap or passageway, is (further) adapted to increase the pressure on the content and/or in the air cavity 32 after firing/actuating the drug delivery device 100 in order to prevent the formation of negative pressure within air cavity 32 which might result in pulling back piston 12 and, thus, formation of vapor and gas bubbles in the container 16.

In particular, mechanism 30, in particular the gap or passageway, allows air to flow back in cavity 32 increasing the pressure in cavity 32, preferably to ambient pressure, and, hence, preventing the piston 12 from moving backwards. E.g. if the user leaves the device 100 cocked, the pressure in cavity 32 will be reduced and/or equal to ambient pressure. In this case, firing/actuating the device 100 will temporarily result in (partial) vacuum or negative pressure in cavity 32, which can be compensated/increased via the gap or passageway.

Particularly preferred, the gap or passageway is located between the piston 33 and cylinder 31. However, other solutions are possible as well, as will be described below.

In the first embodiment, the cylinder 31 is preferably associated with or connected to the cartridge 10 and/or piston 12.

The actuation piston 33 of the mechanism 30 is preferably associated with or connected to the drug delivery device 100 or nebulizer 101, in particular to the lower or bottom case 21 or the like.

The cartridge 10, in particular piston 12 and/or the cylinder, is/are preferably coated and/or comprises/comprise preferably a coating, in particular a PTFE and/or silicone coating, preferably in order to reduce the friction between the piston 12 and the cylinder of said piston/cylinder arrangement.

One preferred aspect is, that the preferably stroke-like movement of the cartridge 10 relative to a housing, such as case 21, and/or within the drug delivery device 100, in particular the movement when tensioning or cocking the drug delivery device 100, is used to actuate the mechanism 30. In particular, the mechanism 30 can be activated or actuated by cocking/tensioning the drug delivery device 100.

Figure 4C:
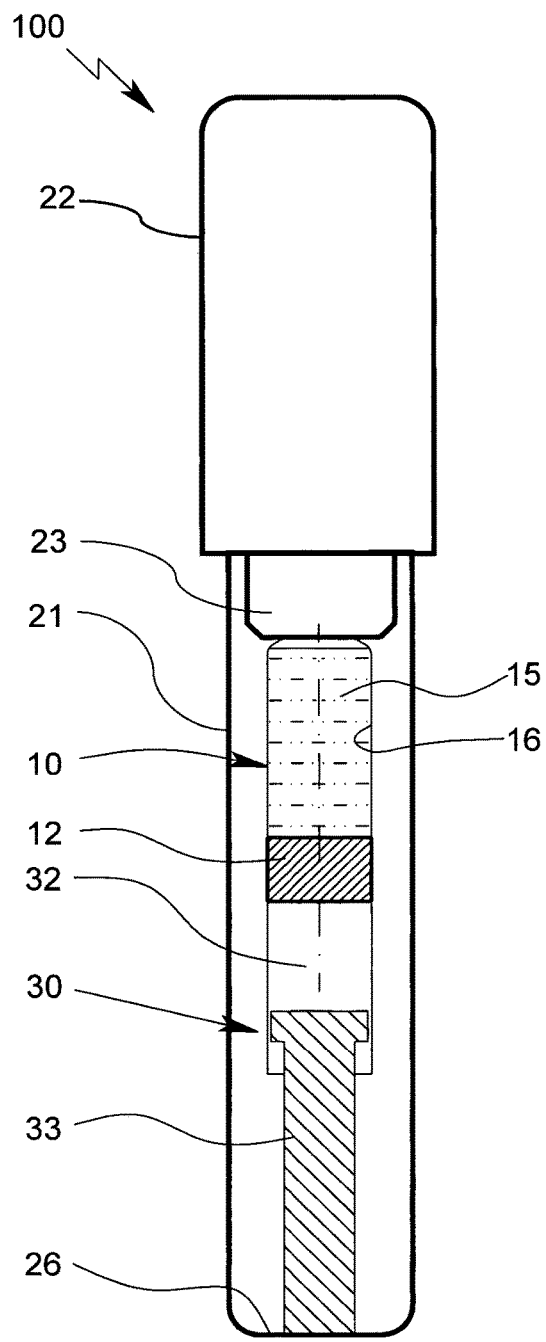
Figure 4D:
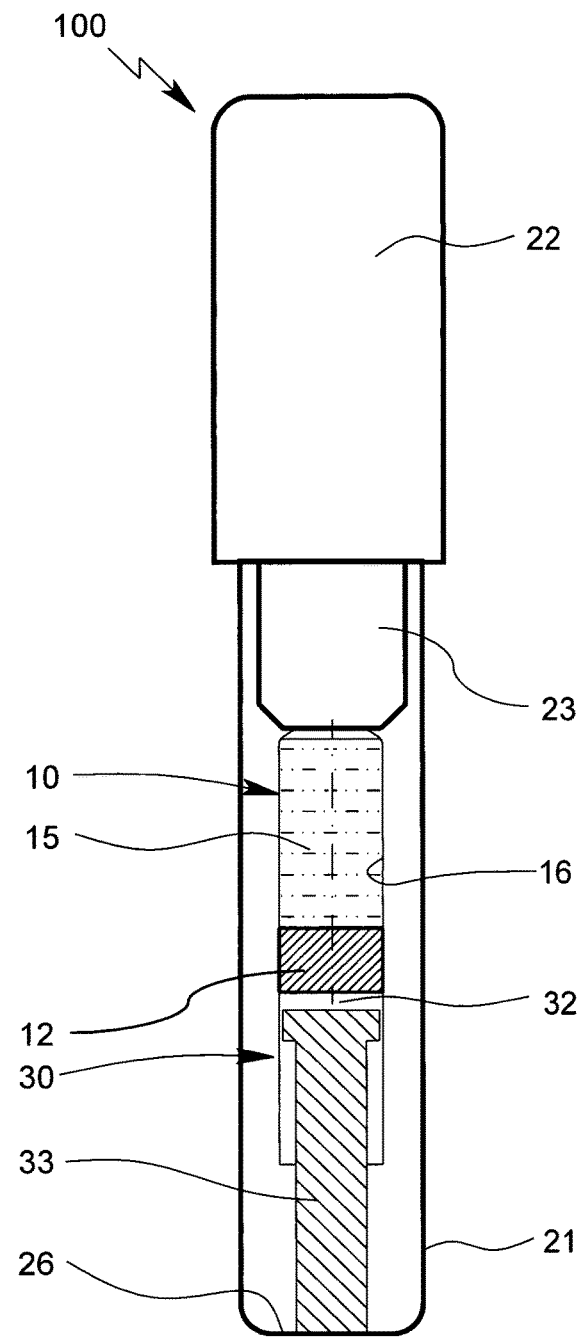

FIGS. 4c and 4d show in similar schematic sections as FIGS. 4a and 4b a second embodiment of the cartridge assembly or drug delivery device 100 according to the present invention.

In FIGS. 4c and 4d the piston 33 forms a seal directly with the walls of the cartridge 10 or its barrel or preferably cylindrical and/or metal case. When the air between the pistons 33 and 12 is pressurized, the piston 12 pressurizes the contents within cartridge 10.

Figure 5A:
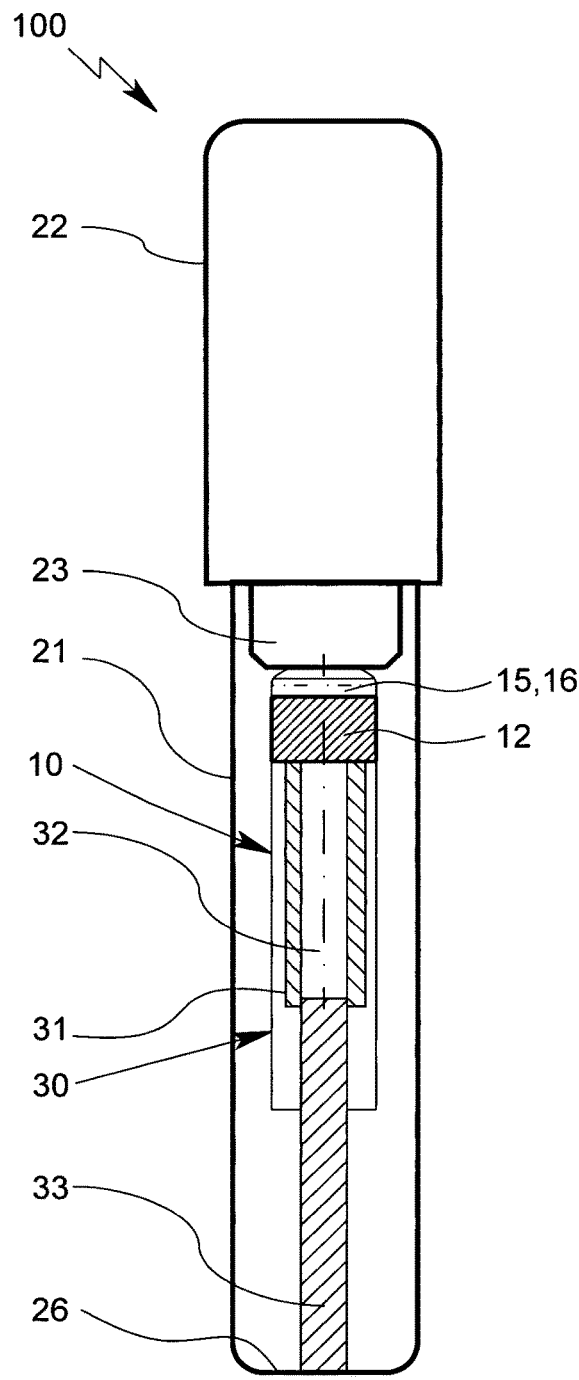
Figure 5B:
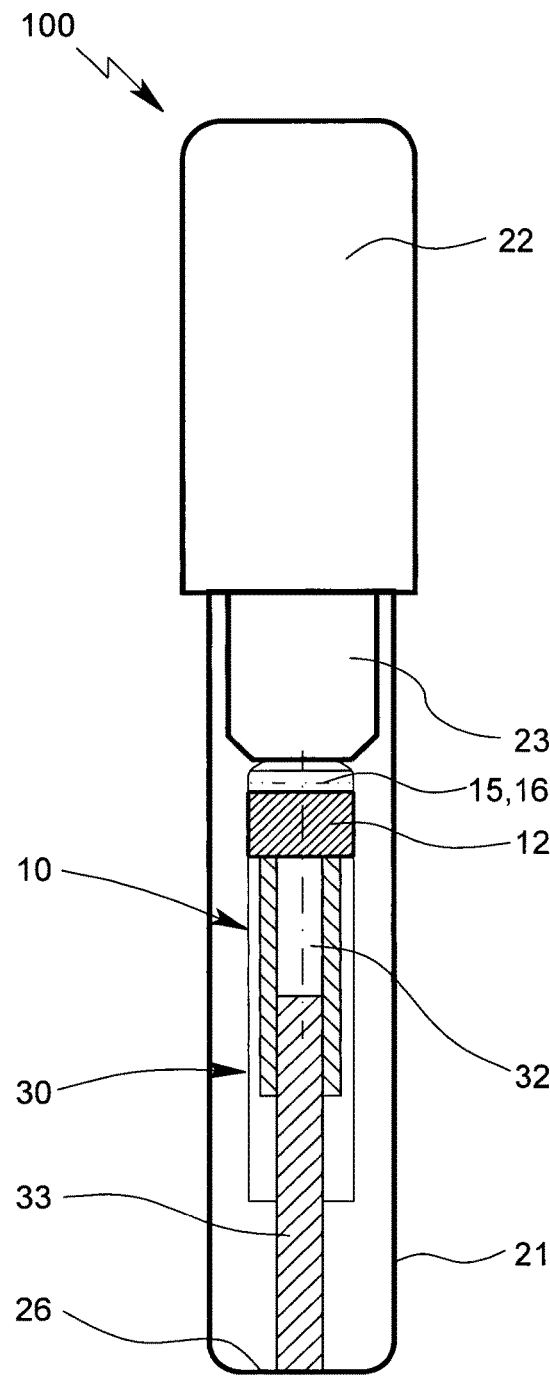

FIGS. 5a and 5b show the same arrangement as FIGS. 4a and 4b with cartridge 10 almost empty.

Preferably, the position of piston 12 relative to the container 16 and/or cartridge outlet corresponds to a (remaining and/or delivered) volume of the liquid 15. Thus, the piston 12 can be embodied as an indicator or a means for displaying information regarding the remaining doses/volume and/or used doses/volume of the drug delivery device 100 to an user.

Preferably, the container 16 and/or the bottom case 21 can be made at least partially of a transparent material. In particular, the container 16 and/or the bottom case 21 comprise/comprises a transparent window to recognize the position of piston 12 from the outside.

Figures 6A, 6B, 6C:
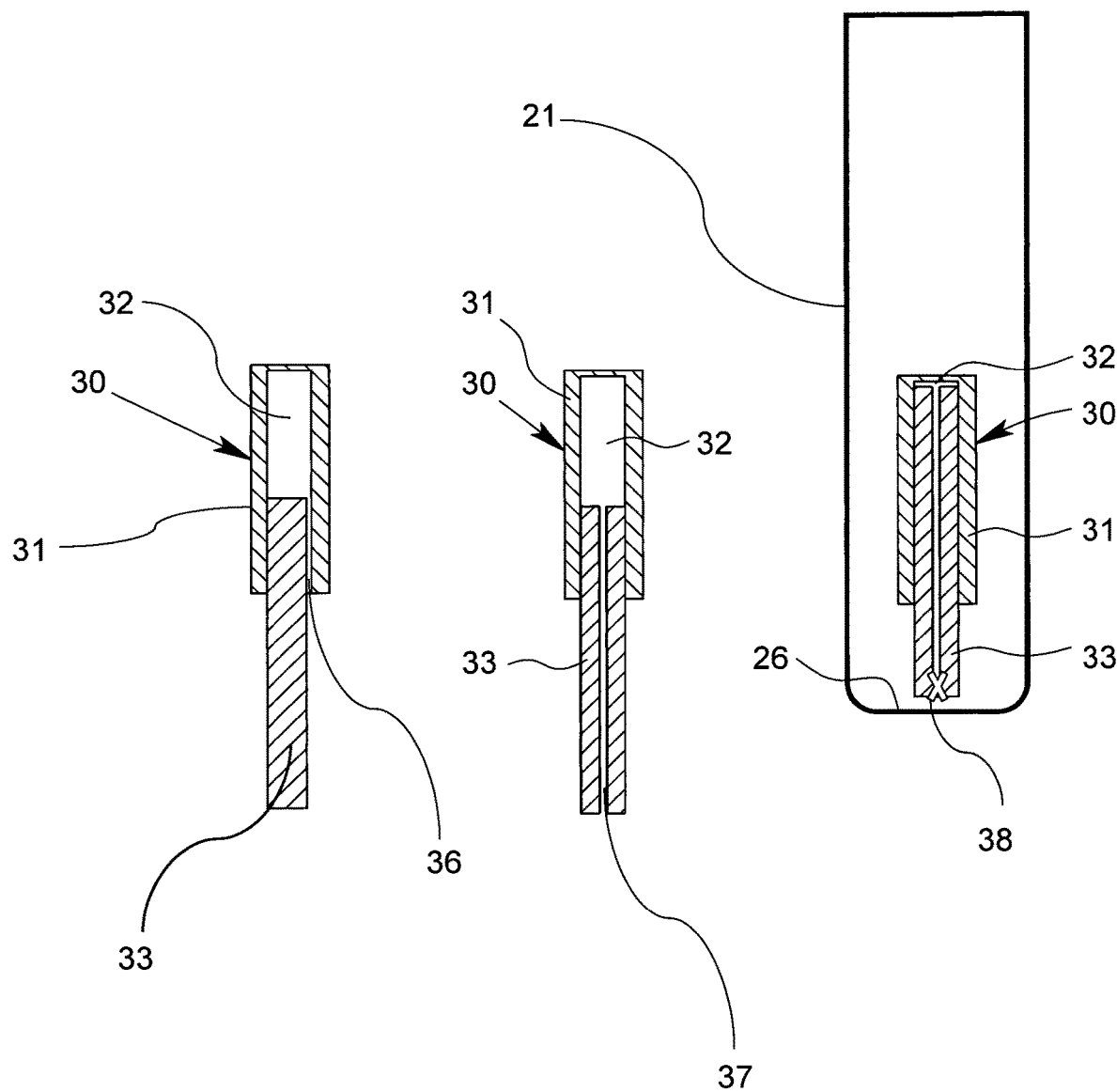

FIGS. 6a to 6c show various embodiments of the invention. In particular, FIGS. 6a to 6c show details or aspects of the mechanism 30 to help collapsing the container, pushing the piston 12 or pressurizing the liquid 15 in very schematic, simplified sections.

In FIG. 6a a small gap or micro gap or passageway 36 forms or creates the air leak pathway. In particular, gap or passageway 36 is an air leak pathway.

Preferably, the gap 36 is formed at the circumference of piston 33 and/or between the piston 33 and the cylinder 31, e.g. by a grove or the like.

In FIG. 6b a capillary 37 provides the air leak pathway. In particular, the capillary 37 is formed by a central opening or bore in piston 33. However, other constructional solutions are possible as well.

In FIG. 6c a valve 38 creates the air leak pathway and is arranged to open when the device 100 is fired to prevent a vacuum or negative pressure forming in the cavity 32 pulling the piston 12 out.

In particular, the valve 38 is realized as a non-return valve. Preferably, the valve 38 is associated to or can close the capillary 37 or any other air leak pathway, optionally even a parallel air leak pathway communicating with air cavity 32.

Figure 6D:
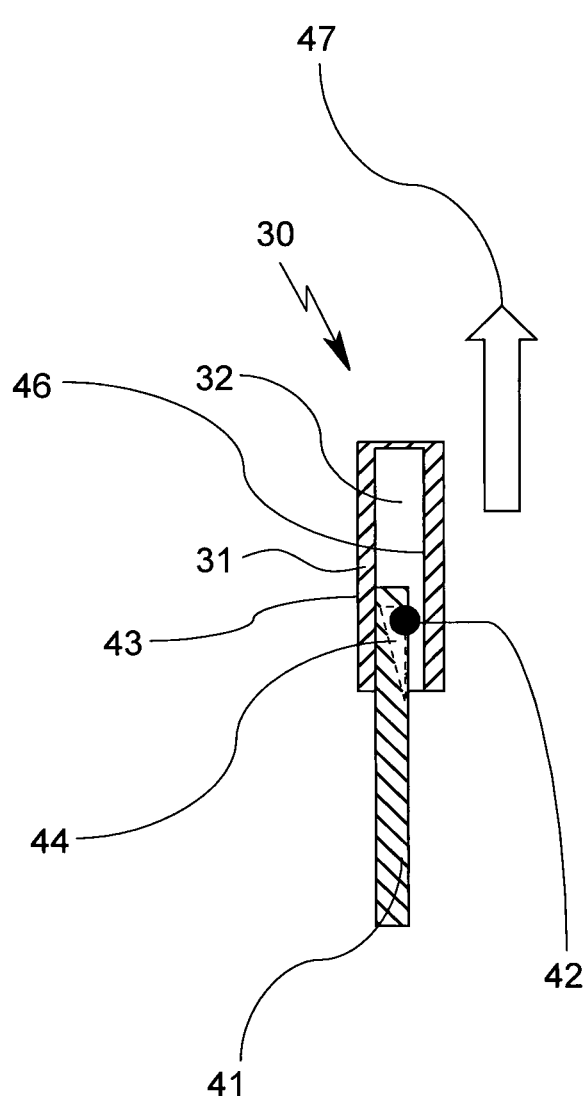
Figure 6E:
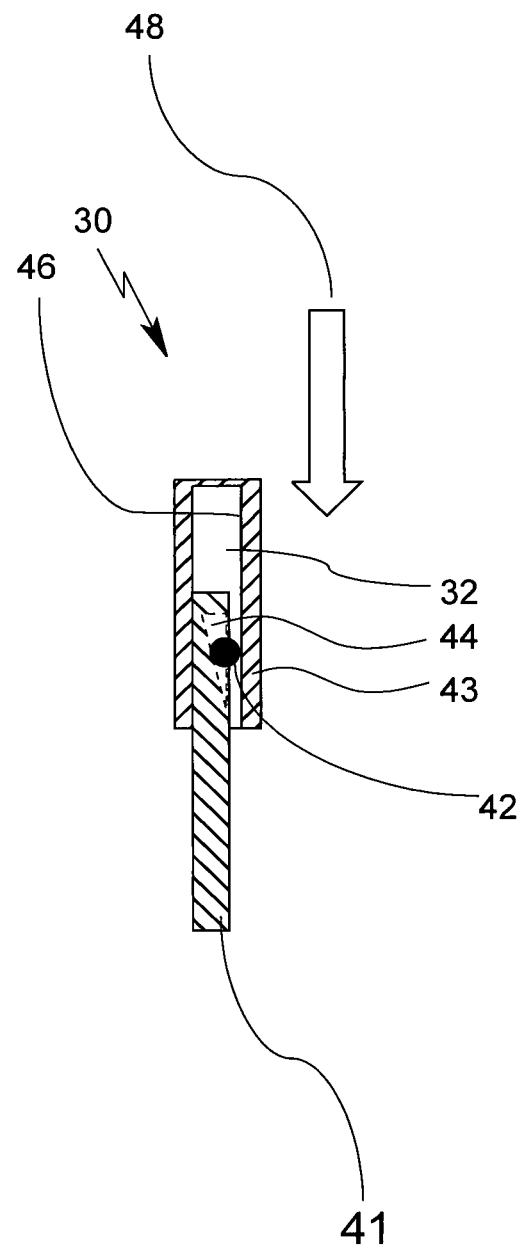

FIGS. 6d and 6e show an alternative arrangement. In particular, FIGS. 6d and 6e show in very schematic sections only the mechanism 30 of a third embodiment of the present invention. Here, the mechanism 30 provides a preferably unidirectional friction engagement/connection for pushing the plunger or piston 12 and/or for compressing or pressurizing the liquid 15 or container 16.

It has to be noted that the associated cartridge 10 and cartridge assembly or drug delivery device 100 are not shown in FIGS. 6d and 6e, but the mechanism 30 can be used together with the cartridge 10 and/or drug delivery device 100 as previously described even if not shown.

Preferably, the mechanism 30 comprises a rod 41 associated to or connected with the drug delivery device 100 or bottom case 21 (not shown), and comprises a counter part or cylinder 43 associated to or connected with the cartridge 10, in particular the piston 12 of the cartridge 10 (not shown). However, other constructional solutions are possible as well.

Preferably, the mechanism 30 provides the friction engagement/connection between the rod 41 and the cylinder 43 only in a (first) direction and/or only when cocking/tensioning the drug delivery device 100. Thus, the rod 41 and the cylinder 43 are frictionally connected to one another in this (first) direction and/or when cocking/tensioning the drug delivery device 100.

In a second, preferably opposite, direction or movement, the friction engagement/connection between the rod 41 and the cylinder 43 does not function or provides an at least essentially reduced force between the rod 41 and cylinder 43. Thus, the rod 41 and the cylinder 43 are movably connected to one another in the (second) direction and/or when firing/actuating the drug delivery device 100.

In particular, the friction engagement/connection between rod 41 and cylinder 43 is unidirectional.

Unidirectional friction preferably means friction and/or a form-fitting connection between at least two components or parts of the device 100, in particular mechanism 30, in a first direction, preferably in such a way that the at least two components or parts are at least essentially immovable to one another, preferably wherein in a second direction—in particular at least essentially opposite to the first direction—no or at least essentially no friction occurs and/or the at least two components or parts are movable at least essentially freely relative to one another.

As shown in FIG. 6d, the (piston) rod 41 has a preferably triangular recess 44 which contains or has or holds—preferably in a form-fit manner—a preferably loose friction element, such as a roll, a sphere or a ball 42.

The friction element is preferably movable within the recess 44 according to the clearance between the friction element and recess 44 and/or cavity wall 46 of cylinder 43.

The depth of recess 44 preferably changes in the axial direction of rod 41. Preferably, the depth of recess 44 increases in the direction towards piston 12, in particular linearly.

Preferably, the friction element or ball 42 is held in place by the recess 44 and the cavity wall 46 of cylinder 43 which is connected to the cartridge piston (not shown).

FIG. 6d shows the mechanism 30 in its rest position and/or while firing/actuating the device 100. FIG. 6e shows the mechanism 30 while being tensioned.

During firing/actuating the device 100 the cartridge 10 or cylinder 43 moves relative to (piston) rod 41 and/or bottom case 21, away from the bottom 26 of case 21 and/or towards connector 23 pulling ball 42 into the deep portion of recess 44. In this way, the friction element or ball 42 is released and/or movable within the recess 44 and does not create friction between rod 41 and wall 46. Thus, the cylinder 43 can be moved relative to rod 41.

During device firing the cartridge 10 and cavity 32 move in the direction of arrow 47 relative to piston 41 pulling ball 42 into the deep portion of recess 44 creating no friction between ball 42 and wall 46 as shown in FIG. 6d.

During loading or tensioning the device 100 the cartridge 10 or cylinder 43 moves downwards relative to rod 41 and/or towards the bottom case 21 and/or closer to the bottom 26 of case 21 clamping and/or squeezing ball 42 between rod 41 and wall 46. In this way, friction between rod 41 and cylinder 43 is created. Thus, cylinder 43 is at least essentially immovable relative to rod 41. In consequence, the cartridge plunger or piston 12 is pushed inwards and/or towards connector 23 and the liquid 15 or container 16 of the cartridge 10 is compressed.

In FIG. 6e the device 100 is being loaded or cocked and the cavity 32 or cylinder 43 moves in the direction of arrow 48 relative to rod 41 squeezing ball 42 between recess 44 and wall 46 creating friction and in effect pushing cartridge plunger or piston 12 inwards and compressing the liquid 15 or container 16 of the cartridge 10 within.

The cavity wall 46 may have a rough surface such as a screw thread surface to increase friction between itself and the ball 42.

More than one cavity 32 and ball 42 may be used. Balls 42 can be replaced with other shapes such as rollers or cylinders or triangular wedges or rings, in particular O-rings, or any other arrangement.

The cartridge piston 12 may be connected to or provided with a ratchet arrangement that only allows it to move in one direction towards the cartridge outlet or septum 14 (FIG. 1). Such a ratchet arrangement is show and explained in FIGS. 11b and 11c.

The ratchet arrangement is adapted to prevent the piston 12 to move downwards and/or closer to the bottom 26 of case 21 and/or away from the cartridge outlet or septum 14, even in the case of vacuum or negative pressure within the cavity 32.

Figure 7A:
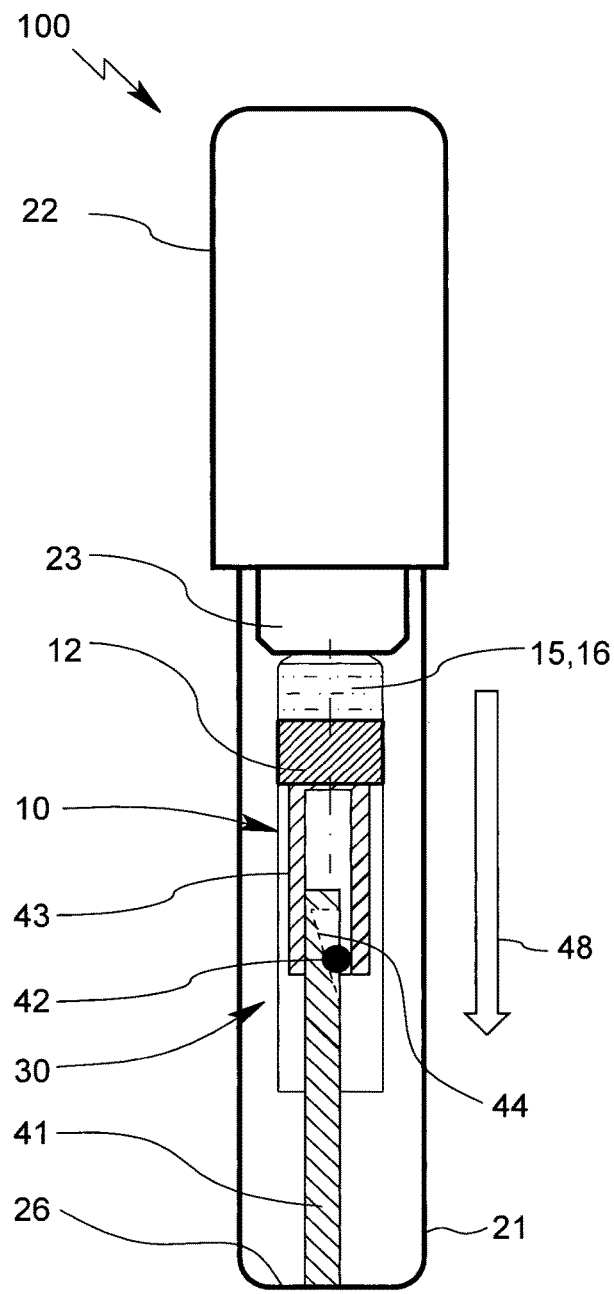
Figure 7B:
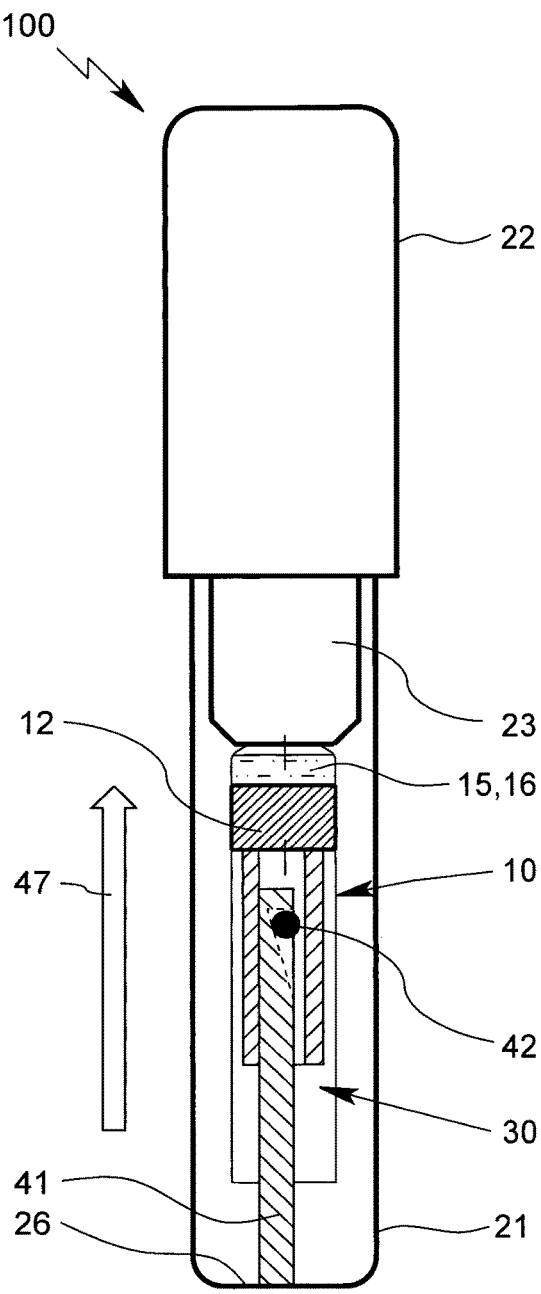

FIGS. 7a and 7b show the cartridge system or mechanism 30 shown in FIGS. 6d and 6e mounted in a device 100.

In FIG. 7a the device 100 is being cocked or loaded preferably with a device spring being compressed ready for drug delivery. The ball 42 gets squeezed/trapped between rod 41 and wall 46 of cylinder 43 and/or creates friction between itself and cylinder 43 and/or between rod 41 and cylinder 43 pushing piston 12 forward and compressing liquid 15 with cartridge 10 when it moves in the direction of arrow 48.

Preferably the ball 42 can be squeezed/trapped between rod 41 and wall 46 in such a way that the cylinder 43 is at least essentially immovable relative to rod 41 and/or frictionally connected to rod 41. Preferably, (further) movement in the direction of arrow 48 pushes piston 12 forward and compresses liquid 15 within cartridge 10.

In FIG. 7b the device 100 is being fired/actuated and a drug dose is delivered. The cartridge 10 or cylinder 43 moves upwards, away from bottom 26 of case 21 and/or towards connector 23. The ball 42, squeezed/trapped between (piston) rod 41 and wall 46, gets released and/or no longer makes friction with the cylinder 43 and does not interfere with the cartridge movement in the direction of arrow 47.

Figure 8A:
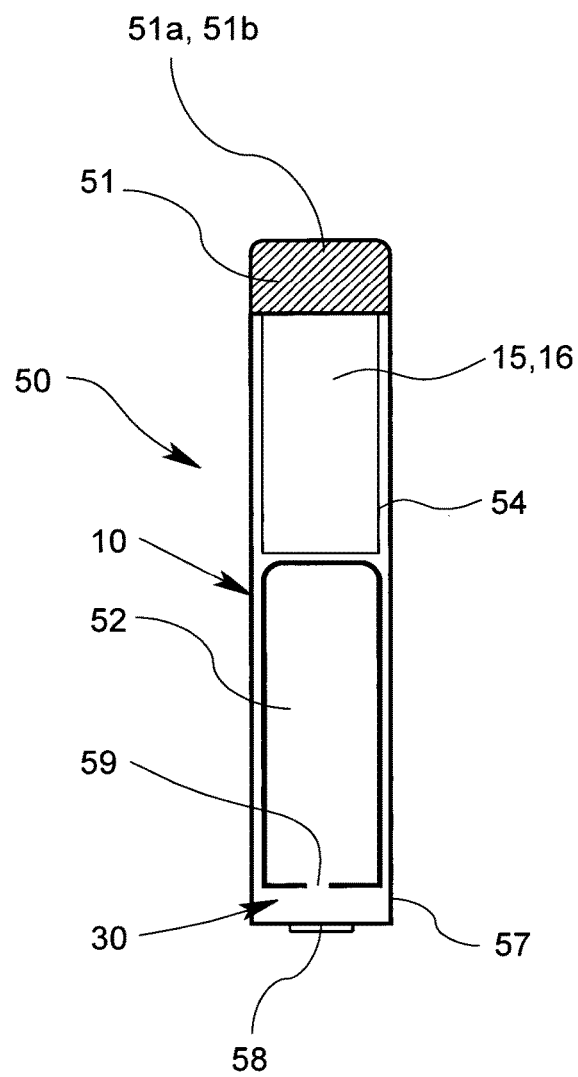

In FIG. 8a an alternative embodiment of the invention is shown. In particular, FIG. 8a shows in a schematic section the cartridge 10 according to a fourth embodiment of the present invention. In particular, the cartridge 10 forms with the mechanism 30 a cartridge assembly 50.

Preferably, the cartridge 10 comprises a collapsible bellows or bag 54 forming the container 16 for the liquid 15.

The cartridge 10 or cartridge assembly 50 preferably contains within or comprises an outer case, container or canister 57, which is preferably rigid and/or made of metal.

The outer container 57 or canister 57 is preferably closed at its fluid outlet by a ferrule or closure 51 which may comprise or consist of a septum or rubber cap 51a and/or a gas barrier foil or seal 51b (only schematically indicated in FIG. 8a). In particular, the seal 51b covers the septum or rubber cap 51a and/or forms a humidity and gas barrier.

Preferably, the cartridge 10 or cartridge assembly 50 and/or mechanism 30 comprises an actuation element, such as a piston 52. Preferably, the actuation element or piston 52 is contained or arranged within the canister 57 and/or comprises an engagement portion or hole 59.

The cartridge assembly 50 or canister 57 comprises preferably an opening in the bottom and/or opposite to the outlet end. The opening is covered preferably by a foil 58 or the like for forming a humidity and gas barrier. Hence, the contents of the bellows or bag 54 are sealed by an outer barrier comprised of the outer container or canister 57 and closures, seals or foils 51, 51b and 58.

Figure 8B:
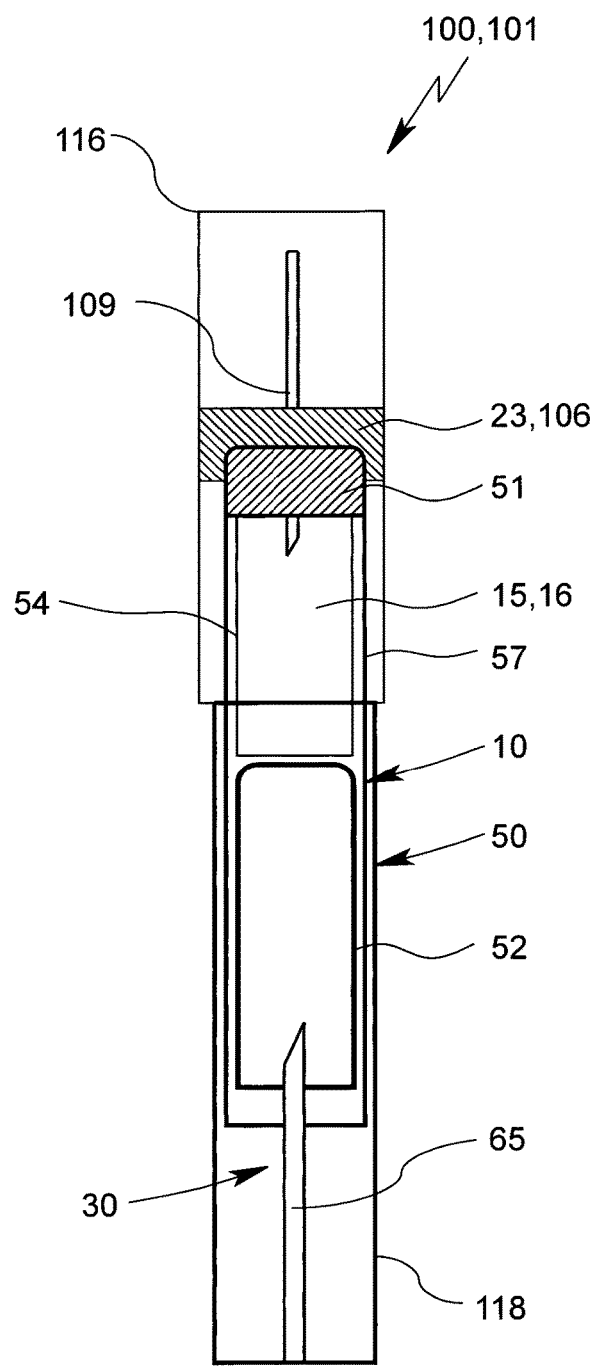

In FIG. 8b the cartridge assembly 50 is shown held inside a drug delivery device 100 or nebulizer device 101. In particular, the drug delivery device 100 comprises a lower casing or lower housing part 118 and/or an upper casing or upper housing part 116.

The cartridge assembly 50 or cartridge 10 is preferably held inside and/or moved within the drug delivery device 100 or nebulizer 101 during operation. In particular, the cartridge 10 is moved axially and/or stroke-like during nebulization in one direction and cocking of the device 100 in the other direction.

A cartridge 10 or cartridge assembly 50 or its outlet end or head 51 is held firmly preferably by the connector 23 such as a holder 106 shown in FIG. 8b or clasp or the like. In particular, a needle or connecting element, such as a conveying tube 109, pierces or opens the ferrule or closure 51, in particular the seal 51b and septum 51a for assessing or connecting the contents or liquid 15 in the container 16 or bag 54 as schematically indicated in FIGS. 8b and 12a.

The mechanism 30 or cartridge assembly 50 and/or the drug delivery device 100 comprises preferably the piercer or an opening or rod or actuation element 65, in particular attached to the lower case or housing part 118. In particular, the piercer or actuation element 65 perforates closure or seal 58 of the housing or canister 57 for allowing atmosphere flowing into the cartridge 10 or cartridge assembly 50 as the container 16 or bellows or bag 54 collapses during operation. In particular, a venting device is formed. However, other constructions or solutions are possible as well.

Figure 8C:
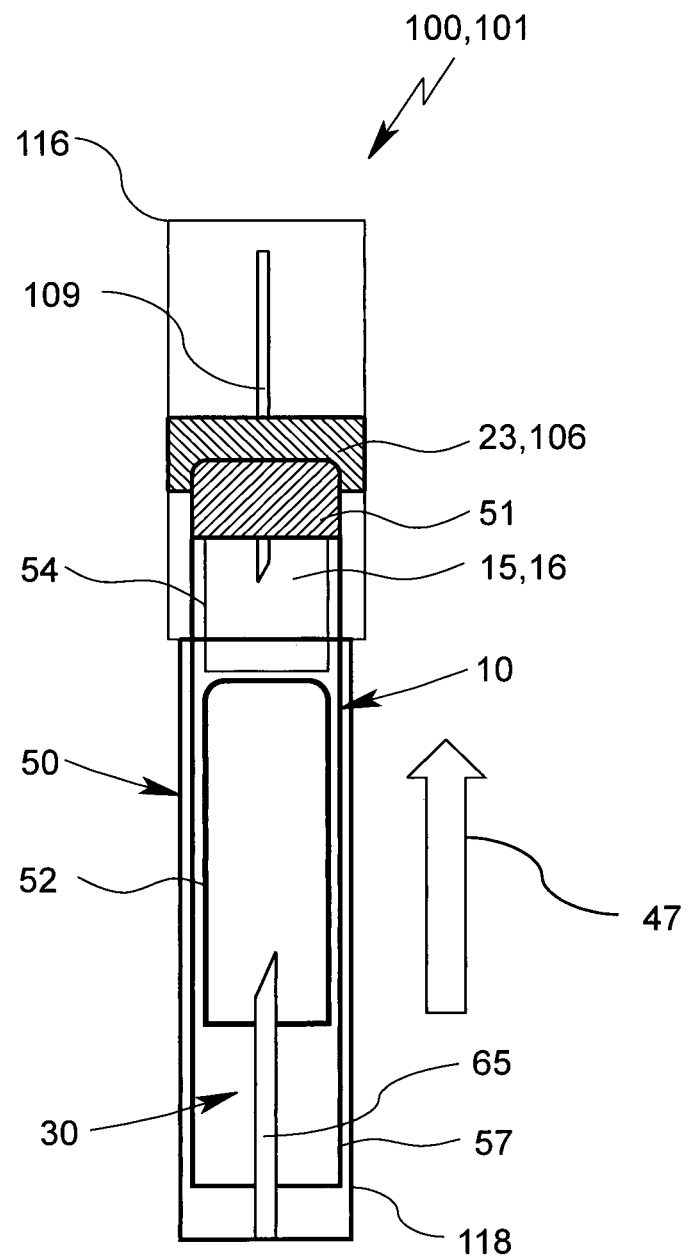

In FIG. 8c the operation of the cartridge 10 and device 100 is shown. The piston 52 moves preferably only in the direction of arrow 47. This is achieved preferably by unidirectional friction or a ratchet mechanism/arrangement or any or any other engagement between the piston 52 and the outer container or canister 57 and preferably unidirectional friction or a ratchet mechanism/arrangement or any other engagement between the piercer or an actuation element 65 and the piston 52. In this way as the bellows or bag 54 collapses piston 52 exerts a pressure by mechanical abutment or via an air spring or air cavity 32 on it during device cocking and bellows or bag 54 is emptied as shown in FIGS. 9a to 9c.

Figure 9A:
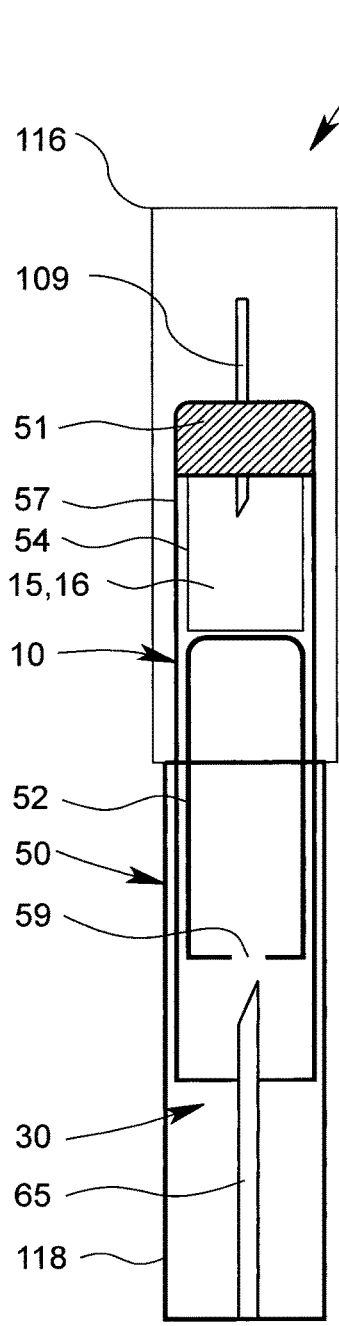
Figure 9B:
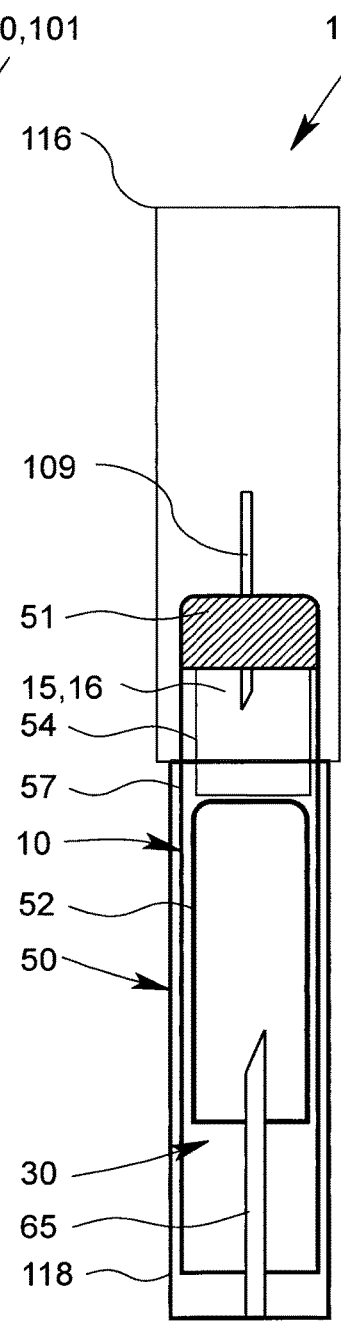
Figure 9C:
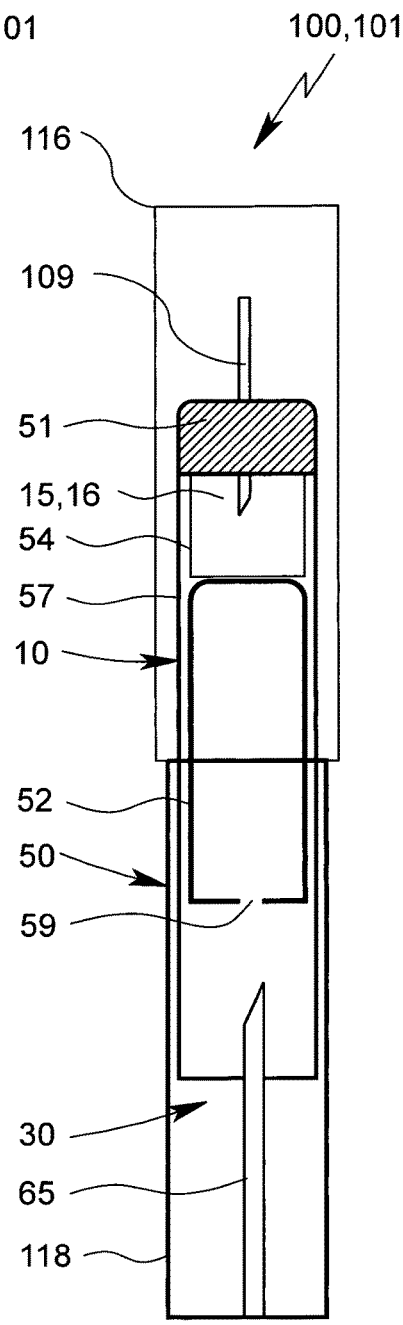

In FIGS. 9a and 9c the atomizing device 100 is shown in its uncocked position. In FIG. 9b it is shown in the cocked position. Needle or connecting element 109 is connected to or is part of a pump or piston and one-way valve arrangement (a respective embodiment is explained later with reference to FIG. 12a). This moves relative to a cylinder when the cartridge 10 or assembly 50 moves downwards relative to lower case 118. The unidirectional friction between piston 52 and canister or housing 57 and the engagement or impact of piercer or actuation element 65 on piston 52 moves the piston 52 upwards or towards the hit of cartridge 10 or container 16 or bellows or bag 54 and, thus, compresses the contents or liquid 15 or container 16, here the bag 54, during cocking of device 100.

Figure 10A:
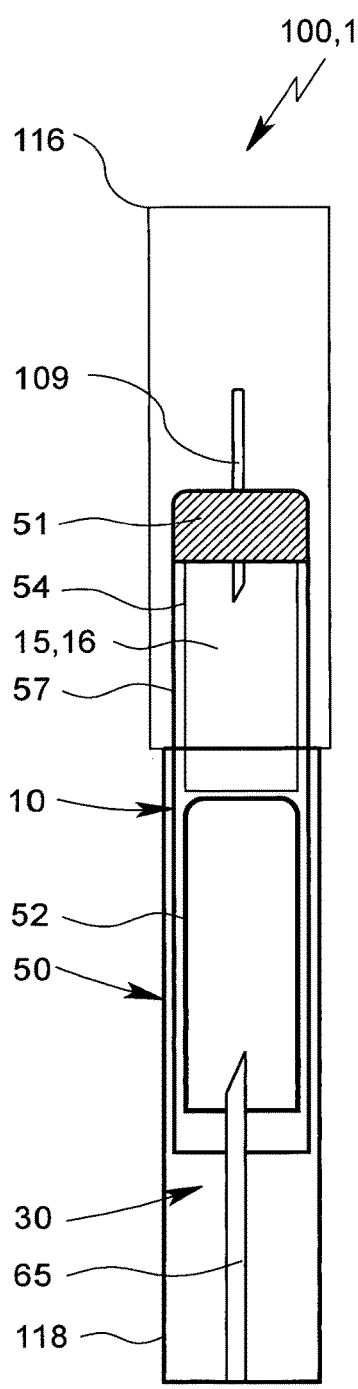
FIG. 10a shows a schematic section of the cartridge assembly or drug delivery device similar to FIGS. 9a and 9c, but with a new unused cartridge.
Figure 10B:
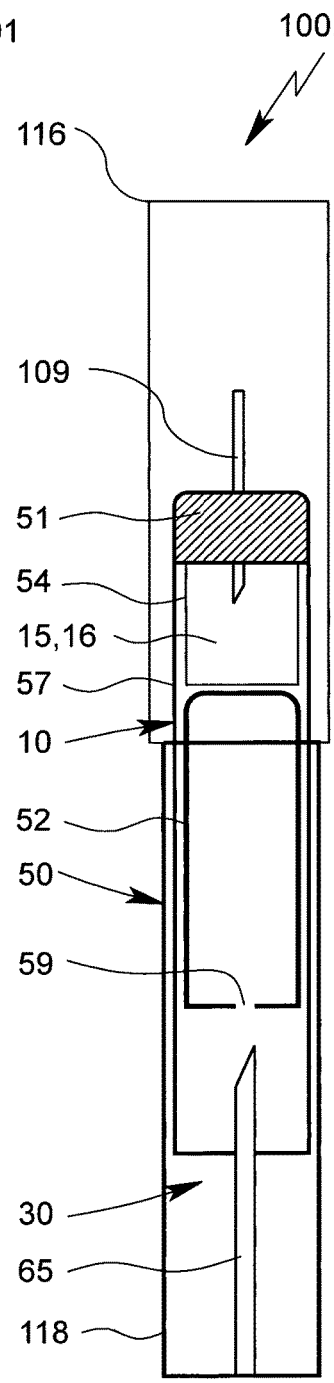
FIG. 10b shows a schematic section of the cartridge assembly or drug delivery device similar to FIGS. 9a and 9c, but with a half used cartridge.
Figure 10C:
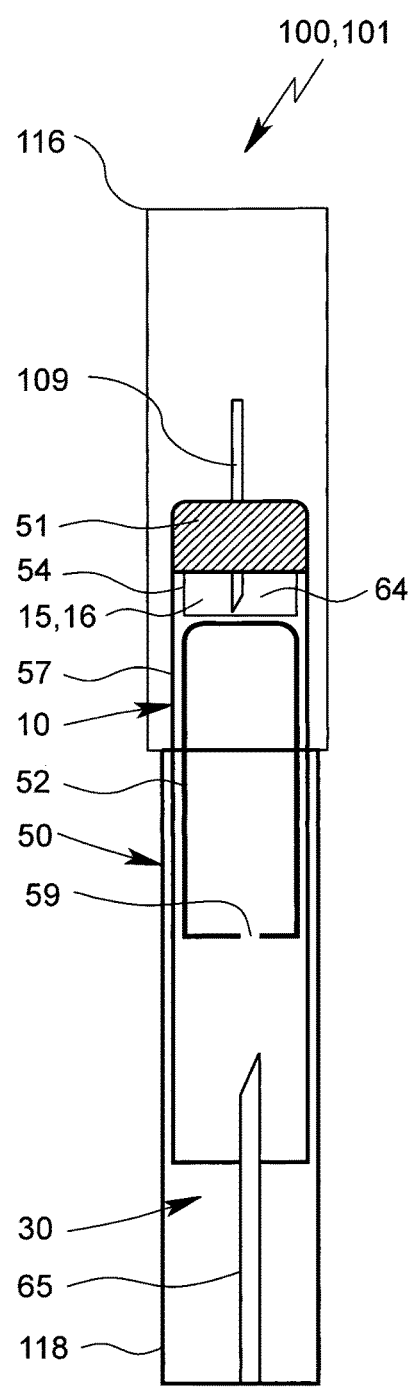
FIG. 10c shows a schematic section of the cartridge assembly or drug delivery device similar to FIGS. 9a and 9c, but with an empty cartridge.

In FIG. 10a the uncocked device 100 is shown with a new unused cartridge 10. In FIG. 10b the uncocked device 100 is shown with a half used cartridge 10 and in FIG. 10c with an empty cartridge 10 with a residual volume or overfill 64. Overfill 64 can be almost eliminated if bellows or bag 54 is designed for this purpose.

The standard cartridge shown in FIGS. 1 to 6 may be used with the unidirectional piston arrangement shown in FIGS. 8 to 10. Likewise the air spring shown in FIGS. 4 to 6 may be used with a bellows or by bag 54 alternatively or in combination.

Figure 11A:
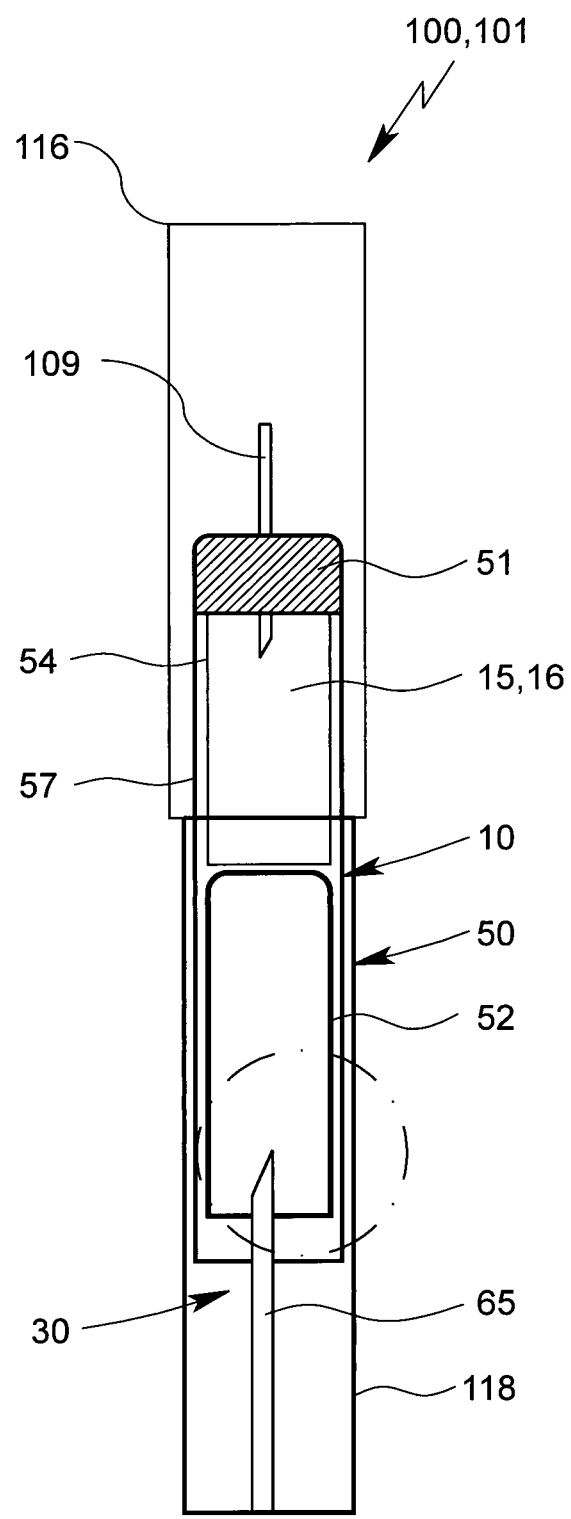
FIG. 11a shows a schematic section of the cartridge assembly or drug delivery device according to the fourth embodiment with a ratchet arrangement as preferred realization of the mechanism to help collapsing the container.
Figure 11B:
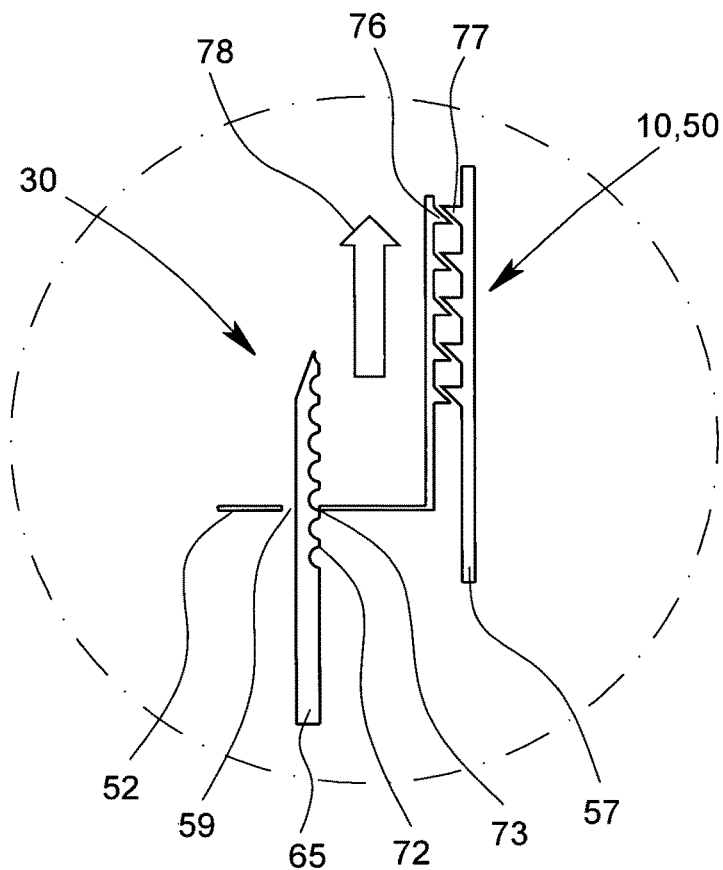
Figure 11C:
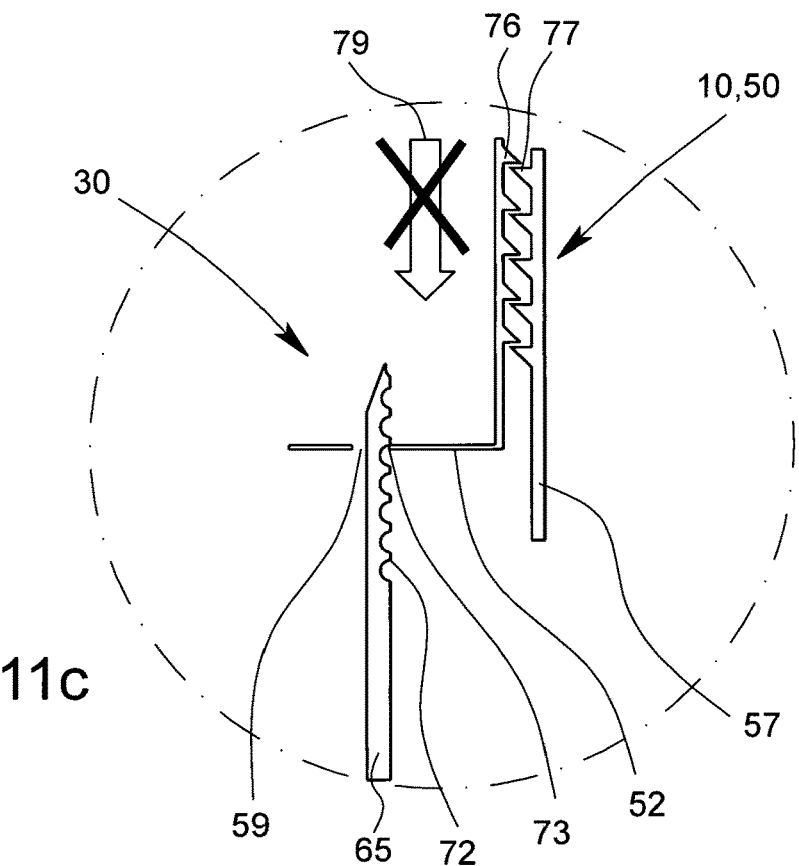

The unidirectional friction may be achieved by many means including for example a ratchet mechanism/arrangement similar to those found in 'tie' wraps and as shown in FIGS. 11b and 11c.

In FIGS. 11a, 11b and 11c an alternative mechanism 30 according to the invention is shown. In particular, FIG. 11a shows in a schematic section similar to FIG. 8a of the cartridge assembly 50 or drug delivery device 100 according to the forth embodiment together with a ratchet arrangement as preferred realization of the mechanism 30 to help collapsing the container 16 and/or prevent the collapsed container to expand again.

It has to be noted that the mechanism 30 can be realized independently from the forth embodiment, in particular combined with any other of the described embodiments.

FIG. 11a shows in a schematic section similar to FIG. 8b the preferred drug delivery device 100. FIGS. 11b and 11c show partial, schematic enlargements of the encircled area of FIG. 11a for explaining a preferred realization and operation of the mechanism 30, cartridge assembly 50 and drug delivery device 100, wherein FIG. 11b shows the operation when the device 100 is cocked and FIG. 11c shows the situation during firing or nebulization.

The piercer, rod or element 65 has preferably rounded teeth marks 72. These engage with a lip or edge 73 on the hole 59 in piston 52 when they travel past or relative to each other. The teeth 72 engage with the edge 73 pushing the piston 52 in the direction of the arrow 78 during cocking as shown in FIG. 11a.

The piston 52 has preferably sharp teeth 76 which engage with opposite preferably sharp teeth 77 on outer canister 57. This engagement form a unidirectional (friction) engagement or ratchet mechanism and allows the piston 52 only to move in the direction of arrow 78, but not in the opposite direction when firing as indicated by arrow 79 in FIG. 11c.

When the device 100 is cocked the rod or element 65 forces the piston 52 up against bellows or bag 54 pressurizing it. When the device 100 is fired the rod or element 65 moves in the opposite direction but cannot drag the piston 52 back as teeth 76 and 77 trap the piston 52 in its new position. The piston 52 remains in its new position preventing the bellows or bag 54 from expanding and preventing the forming of gas and vapor bubbles within the bellows or bag 54.

Other friction materials may be used. For instance teeth 76 and 77 may be replaced by a 'velcro' type material. Teeth 72 and edge 73 may be replaced by a 'tie wrap' type arrangement. The teeth 76 and 77 arrangement or any other ratchet arrangement or unidirectional engagement may be used with the piston 12 in cartridge 10 shown in FIGS. 1 to 6.

It has to be noted that the mechanism 30, in particular the unidirectional engagement or ratchet arrangement, can be adapted to permit a certain expansion of bellow or bag 54 or container 16 and/or movement of piston 52 or 12 towards its initial position. In this way, e.g. thermal expansion of the components or parts of the device 100, in particular of liquid 15, can be compensated preventing internal mechanical stress and/or overpressure within container 16. Preferably, components or parts of the mechanism 30, e.g. teeth 76 and/or 77, are flexible/elastic such that some degree of movement against the unidirectional engagement or ratchet arrangement is possible.

FIG. 12a shows in a schematic section a fifth embodiment of the drug delivery device 100, in particular in the form of a nebulizer 101, thus preferably an inhaler, according to the present invention with a further embodiment of the cartridge 10, mechanism 30 and/or cartridge assembly 50. FIG. 12a shows the device 100 in the rest position. FIG. 12b shows in a partial enlargement of the lower area of FIG. 12a the device 100 in a cocked position.

It has to be noted that the shown drug delivery device 100 or nebulizer 101 can be combined with any one of the other embodiments of the cartridge 10, the mechanism 30 and/or cartridge assembly 50.

The nebulizer 101 is for atomizing the fluid 15, particularly a highly effective pharmaceutical composition, medicament or the like. It is diagrammatically shown in a non-tensioned state or rest position in FIG. 12a. The nebulizer 101 is constructed in particular as a portable inhaler and preferably operates only mechanical and/or without propellant gas.

When the fluid, here the liquid 15, more particularly a pharmaceutical composition, is nebulized, an aerosol is formed or dispensed, which can be breathed in or inhaled by a user. Usually the inhaling is done at least once a day, more particularly several times a day, preferably at set intervals, depending on the complaint or illness from which a patient is suffering.

The nebulizer 101 is provided with or comprises an insertable or replaceable cartridge 10 containing the liquid 15. The cartridge 10 or its container 16 or bag 54 thus forms a reservoir for the liquid 15, which is to be nebulized. Preferably, the cartridge 10 contains multiple doses of liquid 15 or active substance in particular sufficient to provide up to 200 dosage units or doses, for example, i.e. to allow up to 200 sprays or applications. A typical cartridge 10, as disclosed in WO 96/06011 A1, holds e.g. a volume of about 2 to 20 ml.

Further, the number of doses contained in the cartridge 10 and/or the total volume of the liquid 15 contained in the cartridge 10 can vary depending on the liquid 15 or respective medicament and/or depending on the cartridge 10 and/or depending on the necessary medication or the like.

Preferably, the cartridge 10 can be replaced or exchanged, wherein the total number of uses of the nebulizer 101 and thus the number of cartridge 10, which can be used with the same nebulizer 101, is preferably restricted, e.g. to a total number of four or five cartridge 10. WO 2012/162305 A1 discloses additionally such a restriction to the total numbers of cartridge 10 which can be used with the same nebulizer 101.

The cartridge 10 is preferably substantially cylindrical or cartridge-shaped and once the nebulizer 101 has been opened the cartridge 10 can be inserted therein preferably from below and changed if desired. It is preferably of rigid construction, the fluid 102 in particular being held in a collapsible bag 54 in the cartridge 10. In particular, the cartridge 10 comprises a venting opening or hole 122 which is opened before or during first use.

The nebulizer 101 comprises a delivery mechanism, preferably a pressure generator 105, for conveying and nebulizing the liquid 15, particularly in a preset and optionally in an adjustable dosage amount.

The nebulizer 101 or pressure generator 105 comprises preferably a holder 106 for releasably holding the cartridge 10, a drive spring 107 associated to the holder 106, only partly shown, and/or a blocking element 108 preferably in form of or with a button for preferably manual actuation or depressing. The blocking element 108 can catch and block the holder 106 and can be manually operated to release the holder 106 allowing drive spring 107 to expand.

The nebulizer 101 or pressure generator 105 comprises preferably a conveying element, such as a conveying tube 109, a non-return valve, a pressure chamber 111 and/or a nozzle 112 for nebulizing the liquid 15 into a mouthpiece 113.

The completely inserted cartridge 10 is fixed or held in the nebulizer 101 via the holder 106 such that the conveying element fluidically connects the cartridge 10 or its container 16 to the nebulizer 101 or pressure generator 105. Preferably, the conveying tube 109 penetrates into the cartridge 10 or bag 54.

The nebulizer 101 or holder 106 is preferably constructed so that the cartridge 10 can be exchanged.

When the drive spring 107 is axially tensioned in the tensioning process, i.e. when the device 100 is cocked, the holder 106 with the cartridge 10 and the conveying tube 109 are moved downwards in the drawings and liquid 15 is sucked out of the cartridge 10 or container 16 or bag 54 into the pressure chamber 111 of the pressure generator 105 through the non-return valve. In this state, the holder 106 is caught by the blocking element 108 so that the drive spring 107 is kept compressed. Then, the nebulizer 101 is in the tensioned state.

Preferably, the drive spring 107 in tensioned, in particular compressed, in the tensioned/cocked position or state of the nebulizer 101 and/or during withdrawal of the liquid 15, in particular of a dose of liquid 15, from the cartridge 10 or its container 16 or bag 54.

Preferably, the drive spring 107 is released when actuating/firing the nebulizer 101.

Preferably, the drive spring 107 does not (directly) pressurize the liquid 15 in the cartridge 10 or its container 16 or bag 54. In particular, the drive spring 107 is adapted to pressurize (only) the amount of liquid 15, i. e. a drug dose, that has been withdrawn from the container 16 or bag 54, preferably previously and/or by tensioning the nebulizer 101.

During the subsequent relaxation in the nebulization process after actuation or pressing of the blocking element 108 the liquid 15 in the pressure chamber 111 is put under pressure as the conveying tube 109 with its now closed non-return valve is moved back in the pressure chamber 111, here in the drawings upwards, by the relaxation or force of the drive spring 107 and now acts as a pressing ram or piston. This pressure forces the liquid 15 through the nozzle 112, whereupon it is nebulized into the aerosol, as shown in FIG. 1, and, thus, dispensed.

Generally, the nebulizer 101 operates with a spring pressure of 5 to 200 MPa, preferably 10 to 100 MPa on the liquid 15, and/or with a volume of liquid 15 delivered per stroke of 10 to 50 µl, preferably 10 to 20 µl, most preferably about 15 µl. The liquid 15 is converted into or nebulized as aerosol, the droplets of which have an aerodynamic diameter of up to 20 µm, preferably 3 to 10 µm. Preferably, the generated jet spray has an angle of 20° to 160°, preferably 80° to 100°. These values also apply to the nebulizer 101 according to the teaching of the present invention as particularly preferred values.

A user or patient (not shown) can inhale the aerosol, preferably while an air supply can be sucked into the mouthpiece 113 through at least one optional air supply opening 115.

The nebulizer 101 comprises preferably a housing 124 and/or (upper) housing part 116 and optionally a biasing or inner part 117 preferably which is rotatable relative thereto (FIG. 12a) and/or has an upper part and a lower part (FIG. 12a).

The nebulizer 101 or housing 124 comprises preferably a (lower) housing part 118. This part 118 is in particular manually operable, and/or releasable fixed, particularly fitted or held onto the inner part 117, preferably by means of a retaining element 119.

Preferably, the housing parts 116 and 118 and/or other parts form the housing 124 of the nebulizer 101.

In order to insert and/or replace the cartridge 10, preferably the housing 124 can be opened and/or the housing part 118 can be detached from the nebulizer 101, inner part 117 or housing 124.

Generally and preferably, the cartridge 10 can be inserted before the housing 124 is closed and/or before the housing part 118 is connected to the housing 124. The cartridge 10 may be inserted, opened and/or fluidically connected to the delivery mechanism automatically or simultaneously when (completely) connecting the housing part 118 to the housing 124/nebulizer 101 and/or when (completely) closing the housing 124/nebulizer 101. Preferably, the cartridge 10 is open or fluidically connected when tensioning the nebulizer 101 for the first time with the current cartridge 10.

Preferably, the nebulizer 101 or drive spring 107 can be manually activated or tensioned, cocked or loaded, in particular by actuation of an actuation member, here preferably by rotating housing part 118 or any other component.

The actuation member, preferably the housing part 118, can be actuated, here rotated relative to the upper housing part 116, carrying with it or driving the inner part 117. The inner part 117 acts on a gear or transmission to transform the rotation in an axial movement. As a result the drive spring 107 is tensioned in the axial direction by means of the gear or transmission (not shown) formed between the inner part 117, in particular its upper part 117a, and the holder 106 and acting on the holder 106. During tensioning the container 3 is moved axially downwards until the cartridge 10 assumes an end or cocked position as shown in FIG. 12b. In this activated, cocked or tensioned state the drive spring 107 is under tension and can be caught or held by the blocking element 108. During the nebulizing process the container 103 is moved back into its original position (non-tensioned or rest position or state shown in FIG. 12a) by (the force of) the drive spring 107. Thus the cartridge 10 executes a lifting or stroke movement during the tensioning or cocking process and during the firing or nebulizing process.

The housing part 118 preferably forms a cap-like lower housing part and/or fits around or over a lower free end portion of the cartridge 10. As the drive spring 107 is tensioned the cartridge 10 moves with its end portion (further) into the housing part 118 or towards the end face thereof, while an aeration means, such as the axially acting or extending piercer or actuation element 65, preferably arranged in the housing part 118, comes in contact with base 121 of the cartridge 10 and pierces the cartridge 10 or a base seal or foil 58 thereon with a piercing element 122 when the cartridge 10 makes contact with actuation element 65 for the first time, to allow air in or aeration, preferably by opening or piercing venting hole 122. The venting hole 122 allows for pressure compensation inside the cartridge 10 when liquid 15 is drawn from the cartridge 10 during the actuation of the nebulizer 101.

For opening the nebulizer 101 or lower housing part 118, a retaining element 119, preferably formed at or by the inner part 117 can be depressed.

The cartridge 10 or mechanism 30 comprises preferably a piston 33 or 52 in the canister 57, wherein the piston 33, 52 is axially movable by means of the piercer or actuation element 65 which engages or abuts against the piston 33, 52 when cocking the device 100 or nebulizer 101 or when the device 100 or nebulizer 101 is in the cocked or tensioned state as shown in FIG. 12*b*.

Preferably, the actuation element 65 moves the piston 33, 52 against a spring force when cocking the device 100 or nebulizer 101. In the cocked or tensioned state (as shown in FIG. 12*b*), the piston 33, 52 acts on the container 16, in particular on the bag 54 and, thus, on the liquid 15 to help collapsing the bag 54 and/or support with drawl of liquid 15.

The piston 33, 52 can abut directly against the container 16 or bag 54 or can act indirectly via an air spring or air cavity 32 as shown.

Preferably, the piston 33, 52 returns automatically into its lower or initial position shown in FIG. 12*a*, in particular by means of a return mechanism such as a return spring 34 or the like.

When the piercer or actuation element 65 enters through the venting hole 122 through the base 121 into the canister 57 during cocking or tensioning, the piston 33, 52 is pushed towards or against the container 16, bag 54 and/or outlet end or head 51 of the cartridge 10.

Gap or passageway 36 preferably forms or creates an air leak pathway and/or a pressure compensation between air cavity 32 and the atmosphere.

Preferably, the actuation element 65 does not sealingly engage with the sides of the venting hole 122 when it enters through the venting hole 122.

Preferably, the actuation element 65 and/or the sides of the venting hole 122 comprise a (longitudinal) channel (or an annular gap between actuation element 65 and sides of the venting hole 122) or the like, so that the ambient pressure is always on both sides of the venting hole 122 once the venting hole 122 has been opened. Thus, the passageway 36 can be arranged inside the cartridge 10 (preferably at or within the piston 33, 52) and can create an air leak pathway even in the cocked or tensioned state of the nebulizer 101.

In particular, gap or passageway 36 is adapted to reduce the pressure within cavity 32 after tensioning of the mechanism 30 or device 100, preferably in order to prevent or minimize leakage of liquid 15 from container 16 during non-use of the device 100. Preferably, gap or passageway 36 is further adapted to increase the pressure within cavity 32 while or after firing/actuating of the mechanism 30 or device 100, preferably in order to prevent negative pressure or vacuum within cavity 32. Reference is made to the description of FIG. 4 to FIG. 11.

In the fifth embodiment, the mechanism 30 comprises preferably the piston 33, 52, in particular movably held within the canister 57, the optional return mechanism such as return spring 34, the optional air cavity 32 and/or the actuation element 65 preferably forming or also acting as a piercer.

Unlike freestanding equipment or the like the proposed nebulizer 101 is preferably designed to be portable and in particular is a mobile hand operated device.

The proposed solution may, however, be used not only in the nebulizers 101 specifically described here but also in other nebulizers or inhalers, e.g. powder inhalers or so-called metered dose inhalers.

Preferably, the content of the nebulizer 101 or device 100, in particular cartridge 10 or container 16, is a liquid 15, as already mentioned, especially an aqueous pharmaceutical formulation or an ethanolic pharmaceutical formulation. However, it may also be some other pharmaceutical formulation, a suspension or the like.

According to an alternative embodiment the content may also comprise particles or powder. In this case, instead of the expulsion nozzle 112, some other kind of supply device may be provided, especially an expulsion opening (not shown) or a supply channel (not shown) for supplying the content to or powder or the like into the mouthpiece 113. The optional air supply opening 115 then serves to supply ambient air preferably in parallel so as to general or allow an airflow with a sufficient volume for breathing in or inhaling through the mouthpiece 113.

If necessary the content may also be atomized by means of a propellant gas.

Preferred ingredients and/or formulations of the preferably medicinal content are listed in particular in WO 2009/115200 A1, preferably on pages 25 to 40, or in EP 2 614 848 A1, paragraphs 0040 to 0087, which are incorporated herewith by reference. In particular, these may be aqueous or non-aqueous solutions, mixtures, formulations containing ethanol or free from any solvent, or the like.

Individual aspect and features of the invention or its embodiments can be realized independently of one another, but also in any combination with one another. In particular, aspects of the present invention described with reference to FIGS. 4 to 12 can be combined with any aspects and features discussed referring to FIGS. 1 to 3.

| List of references numerals: | |
|---|---|
| 10 | cartridge |
| 11 | body |
| 12 | piston |
| 13 | crimp |
| 14 | septum |
| 15 | liquid |
| 16 | container |
| 21 | bottom case |
| 22 | top case |
| 23 | connector |
| 25 | arrow |
| 26 | bottom |
| 27 | spring |
| 30 | mechanism |
| 31 | cylinder |
| 32 | air cavity |
| 33 | piston |
| 34 | return |
| 36 | passageway |
| 37 | capillary |
| 38 | valve |
| 41 | rod |
| 42 | ball |
| 43 | cylinder |
| 44 | recess |
| 46 | wall |

| List of references numerals: | |
|---|---|
| 47 | arrow |
| 48 | arrow |
| 50 | cartridge assembly |
| 51 | closure/head |
| 51a | rubber cap |
| 51b | seal |
| 52 | piston |
| 54 | bag |
| 57 | canister |
| 58 | foil |
| 59 | hole |
| 64 | overfill |
| 65 | actuation element |
| 71 | rod |
| 72 | teeth marks |
| 73 | edge |
| 76 | teeth |
| 77 | teeth |
| 78 | arrow |
| 79 | arrow |
| 100 | drug delivery device |
| 101 | nebulizer |
| 105 | pressure generator |
| 106 | holder |
| 107 | drive spring |
| 108 | blocking element |
| 109 | conveying tube |
| 111 | pressure chamber |
| 112 | nozzle |
| 113 | mouthpiece |
| 115 | air supply opening |
| 116 | upper housing part |
| 117 | inner part |
| 118 | housing part (lower part) |
| 119 | retaining element |
| 121 | base |
| 122 | venting hole |
| 124 | nebulizer housing |

The invention claimed is:

1. A drug delivery device (100) for a liquid (15) containing a drug, in solution or suspension, comprising:
a cartridge (10) comprising a collapsible and/or compressible container (16) having a variable volume and with the liquid (15) as content,
a mechanism (30) operable to collapse and/or compress the container (16) to urge a reduction in the variable volume of the compressible container (16) and concurrently to pressurize the content during withdrawal of the content from the container (16),
wherein the drug delivery device is adapted to be cocked and then released to nebulize a dose of the content from the container (16) to a patient,
wherein the mechanism (30) is actuated when the drug delivery device (100) is cocked, such that the mechanism (30) only activates the urging in reduction in the variable volume of the compressible container (16), and pressurizes of the content, when the drug delivery device is cocked during withdrawal of the content from the container (16), whereby cocking the drug delivery device includes withdrawal of the dose of the content from the container (16) while the mechanism (30) facilitates pressurizing the content during such withdrawal,
wherein the mechanism (30) is adapted to prevent the container (16) from expanding after collapsing while the drug delivery device is cocked, and
wherein the mechanism (30) is adapted to compensate the pressure within the cartridge (10) to decrease pressure within the container (16) to an atmospheric pressure after release and nebulization of the dose of the content.

2. The drug delivery device according to claim 1, wherein the mechanism (30) includes a movable piston within a cylinder.

3. The drug delivery device according to claim 2, wherein at least one of the piston (12) and the cylinder comprises a coating in order to reduce friction between the piston (12) and the cylinder.

4. The drug delivery device according to claim 1, wherein the container is a collapsible bellows or bag (54).

5. The drug delivery device according to claim 1, wherein the mechanism (30) comprises an air spring.

6. The drug delivery device according to claim 5, wherein the air spring comprises an air cavity (32), in which air is compressed when the drug delivery device (100) is cocked, and in which air is expanded when the drug delivery device (100) is released.

7. The drug delivery device according to claim 6, wherein the mechanism (30) comprises a valve and/or an air leakage pathway associated with the air spring or air cavity (32) so that the air spring pressurizes the content temporarily during withdrawal of the content from the container (16).

8. The drug delivery device according to claim 7, wherein the valve is arranged within the air leakage pathway and/or controls an air flow through the air leakage pathway.

9. The drug delivery device according to claim 5, wherein the mechanism (30) comprises a valve and/or an air leakage pathway associated with the air spring such that the air spring pressurizes the content temporarily during withdrawal of the content from the container (16).

10. The drug delivery device according to claim 9, wherein the valve is arranged within the air leakage pathway and/or controls an air flow through the air leakage pathway.

11. The drug delivery device according to claim 1, wherein the mechanism (30) pushes a cartridge plunger or piston (12) when the drug delivery device (100) is cocked.

12. The drug delivery device according to claim 11, wherein the mechanism (30) provides a unidirectional friction engagement for pushing the cartridge plunger or piston (12) and pressurizing the liquid (15).

13. The drug delivery device according to claim 1, wherein the mechanism (30) comprises a friction element having a ball (42) for acting on a piston (12) or on the container (16) when the drug delivery device (100) is cocked.

14. The drug delivery device according to claim 1, wherein the mechanism (30) comprises a ratchet arrangement to prevent the container (16)) from expanding after collapsing while the drug delivery device is cocked.

15. The drug delivery device according to claim 1, wherein the cartridge (10) and the mechanism (30) form a cartridge assembly (50).

16. The drug delivery device according to claim 1, wherein the drug delivery device (10) is or forms a nebulizer (101).

17. The drug delivery device according to claim 1, wherein the mechanism (30) includes a force providing element operating to cause the activation and urge the reduction in the variable volume of the compressible container (16), and pressurizes of the content, when the drug delivery device is cocked.

18. The drug delivery device according to claim 17, wherein:

the force providing element engages and moves a wall element of the container in such a way as to provide the urge in reduction in the variable volume of the compressible container (16), and pressurizes of the content when the drug delivery device is cocked, and the force providing element disengages from the wall element of the container to permit the pressure within the container (16) to reduce to atmospheric pressure after release and nebulization of the dose of the content.

19. The drug delivery device according to claim 18, wherein:

the force providing element is an air spring mechanism including an air cavity (32) located adjacent to the wall element, where air trapped within the air cavity (32) is compressed and produces a force that causes the engagement and movement of the wall element to provide the urge in reduction in the variable volume of the compressible container (16), and pressurizes of the content when the drug delivery device is cocked, and the air within the cavity (32) is permitted to expand such that the force is released and the force providing element disengages from the wall element of the container to permit the pressure within the container (16) to reduce to atmospheric pressure after release and nebulization of the dose of the content.

20. The drug delivery device according to claim 18, wherein:

the force providing element is a mechanical spring element (27) located adjacent to the wall element, where mechanical spring element (27) is compressed and produces a force that causes the engagement and movement of the wall element to provide the urge in reduction in the variable volume of the compressible container (16), and pressurizes of the content when the drug delivery device is cocked, and the mechanical spring element (27) is permitted to expand such that the force is released and the force providing element disengages from the wall element of the container to permit the pressure within the container (16) to reduce to atmospheric pressure after release and nebulization of the dose of the content.

* * * * *

UNITED STATES PATENT AND TRADEMARK OFFICE
CERTIFICATE OF CORRECTION

PATENT NO. : 11,207,474 B2
APPLICATION NO. : 15/327836
DATED : December 28, 2021
INVENTOR(S) : Stephen Terence Dunne Page 1 of 1

It is certified that error appears in the above-identified patent and that said Letters Patent is hereby corrected as shown below:

In the Claims

In Claim 1, Column 17, Line 56, change "pressurizes of" to --pressurizes--;
In Claim 17, Column 18, Line 61, change "pressurizes of" to --pressurizes--;
In Claim 18, Column 19, Line 1, change "pressurizes of" to --pressurizes--;
In Claim 19, Column 19, Line 15, change "pressurizes of" to --pressurizes--; and
In Claim 20, Column 20, Line 11, change "pressurizes of" to --pressurizes--.

Signed and Sealed this
Twenty-sixth Day of April, 2022

Katherine Kelly Vidal
*Director of the United States Patent and Trademark Office*